US007171263B2

(12) United States Patent
Darvish et al.

(10) Patent No.: US 7,171,263 B2
(45) Date of Patent: *Jan. 30, 2007

(54) DRUG DELIVERY DEVICE

(75) Inventors: Nissim Darvish, Hof-Hacarmel (IL); Itzhak (Itsik) Shemer, Stockholm (SE)

(73) Assignee: Impulse Dynamics NV, Curacao (AN)

( * ) Notice: Subject to any disclaimer, the term of this patent is extended or adjusted under 35 U.S.C. 154(b) by 711 days.

This patent is subject to a terminal disclaimer.

(21) Appl. No.: 10/048,803

(22) PCT Filed: Dec. 13, 2000

(86) PCT No.: PCT/IL00/00832

§ 371 (c)(1),
(2), (4) Date: Jun. 14, 2002

(87) PCT Pub. No.: WO01/93951

PCT Pub. Date: Dec. 13, 2001

(65) Prior Publication Data

US 2002/0183682 A1     Dec. 5, 2002

Related U.S. Application Data

(63) Continuation-in-part of application No. 09/980,908, filed as application No. PCT/IL00/00319 on Jun. 4, 2000.

(60) Provisional application No. 60/137,553, filed on Jun. 4, 1999.

(51) Int. Cl.
*A61N 1/30* (2006.01)
(52) U.S. Cl. .................................................. 604/20
(58) Field of Classification Search .............. 604/20, 604/21, 65, 67; 424/422; 607/3, 9, 39, 40
See application file for complete search history.

(56) References Cited

U.S. PATENT DOCUMENTS 4,164,216 A     8/1979   Person (Continued)

FOREIGN PATENT DOCUMENTS

WO     WO 92/00716     1/1992

(Continued)

OTHER PUBLICATIONS

Antman,E.M. et al.; "Treatment of 150 Cases of Life-Threatening Digitals Intoxication with Digoxin-Specific Fab Antibody Fragments;"Jun. 1990;Circulation;vol. 81;No. 6; pp. 1744-1752.

(Continued)

*Primary Examiner*—George Manuel
(74) *Attorney, Agent, or Firm*—Ehrlich & Fenster

(57) ABSTRACT

Electrical treatment apparatus (100) for use with an associated molecule source, comprising: at least one electrode (106); a power source (120) for electrifying said at least one electrode; and a controller, which is programmed to activate the power source (120) to selectively electrify said at least one electrode (106) to apply at least one electric field including a transport effect for transporting a molecule in a desired manner and a non-excitatory control effect for controlling the activity of at least a part of a non-cardiac excitable tissue, said programming selected to achieve a desired provision of said molecule into said at least a part of an excitable tissue or associated vasculature, said desired provision being at least assisted by an interaction between the transport effect and the control effect.

80 Claims, 4 Drawing Sheets

U.S. PATENT DOCUMENTS

| | | | |
|---|---|---|---|
| 4,273,114 A | | 6/1981 | Barkalow et al. |
| 5,026,397 A | * | 6/1991 | Aoki et al. ............... 424/422 |
| 5,087,243 A | | 2/1992 | Avitall |
| 5,236,413 A | | 8/1993 | Feiring |
| 5,282,785 A | | 2/1994 | Shapland et al. |
| 5,286,254 A | | 2/1994 | Shapland et al. |
| 5,327,887 A | | 7/1994 | Nowakowski |
| 5,386,837 A | | 2/1995 | Sterzer |
| 5,387,419 A | | 2/1995 | Levy et al. |
| 5,415,629 A | | 5/1995 | Henley |
| 5,419,763 A | | 5/1995 | Hildebrand |
| 5,445,609 A | * | 8/1995 | Lattin et al. ............... 604/20 |
| 5,458,568 A | | 10/1995 | Racchini et al. |
| 5,499,971 A | | 3/1996 | Shapland et al. |
| 5,501,662 A | | 3/1996 | Hofmann |
| 5,634,899 A | | 6/1997 | Shapland et al. |
| 5,779,661 A | | 7/1998 | Stephen et al. |
| 5,807,306 A | | 9/1998 | Shapland et al. |
| 5,865,787 A | | 2/1999 | Shapland et al. |
| 6,041,252 A | | 3/2000 | Walker et al. |
| 6,057,374 A | | 5/2000 | Huntington et al. |
| 6,071,305 A | | 6/2000 | Brown et al. |
| 6,086,582 A | | 7/2000 | Altman et al. |
| 6,292,704 B1 | | 9/2001 | Malonek et al. |
| 6,298,268 B1 | | 10/2001 | Ben-Haim et al. |
| 6,634,895 B2 | | 10/2003 | Agro |
| 6,949,081 B1 | * | 9/2005 | Chance ............... 604/67 |
| 7,092,753 B2 | * | 8/2006 | Darvish et al. ............... 604/21 |

FOREIGN PATENT DOCUMENTS

| | | |
|---|---|---|
| WO | WO 95/08316 | 3/1995 |
| WO | WO 97/25098 | 7/1997 |
| WO | WO 98/15317 | 4/1998 |
| WO | WO 99/03533 | 1/1999 |
| WO | WO 99/24110 | 5/1999 |
| WO | WO 99/29307 | 6/1999 |
| WO | WO 99/55360 | 11/1999 |
| WO | WO 99/59548 | 11/1999 |
| WO | WO 00/16741 | 3/2000 |
| WO | WO 00/53257 | 9/2000 |
| WO | WO 00/74773 | 12/2000 |

OTHER PUBLICATIONS

Cano, N.J. et al.; "Dose-Dependent Reversal of Digoxin-Inhibited Activity of an In-Vitro Na+K+ATPase Model by Digoxin-Specific Antibody;"May 1996;Toxicology Letters; vol. 85; No. 2; pp. 107-1011.

Gussoni,E. et al.; "Dystrophin Expression in the MDX Mouse Restored by Stem Cell Transplantation;" Sep. 23, 1999; Nature; vol. 401; No. 6751; pp. 390-394.

Moran,R.J. et al.; "Digoxin-Specific Fab Fragments Impair Renal Function in the Rat;" 1994; Journal of Pharmacy and Pharmacology;vol. 46; No. 10; pp. 854-856.

Patterson, C. et al.; "Therapeutic Angiogenesis—The New Electrophysiology?;"May 25, 1999; Circulation;1999 American Heart Association, Inc; pp. 2614-2616.

Shumaik, G. M. et al; "Oleander Poisoning ; Treatment with Digoxin-Specific Fab Antibody Fragments;"Jul. 1988; Annals of Emergency Medicine; vol. 17;No. 7;pp. 732-735.

Sukhorukov,V.L. et al.; "The Effect of Electrical Deformation Forces on the Electropermeabilization of Erythrocyte Membranes in Low- and High-Conductivity Media;" 1998; The Journal of Membrane Biology; vol. 163; pp. 235-245.

Tsong, T.Y.; "Electroporation of Cell Membranes;"Aug. 1991; pp. 297-306; Biophysical Journal; vol. 60.

* cited by examiner

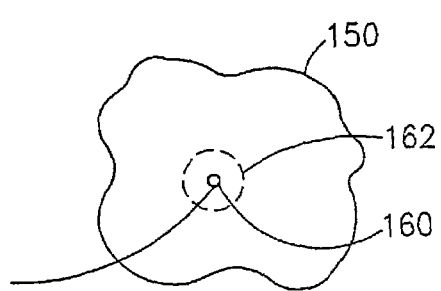
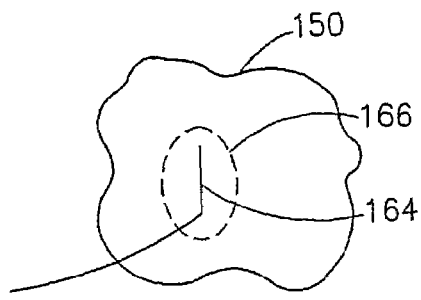
FIG.3A                FIG.3B
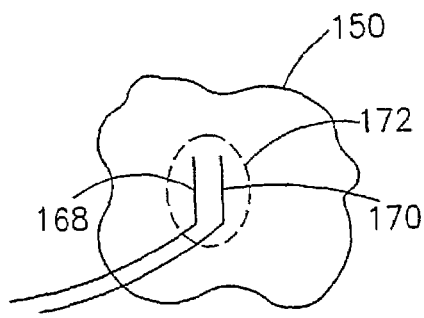
FIG.3C
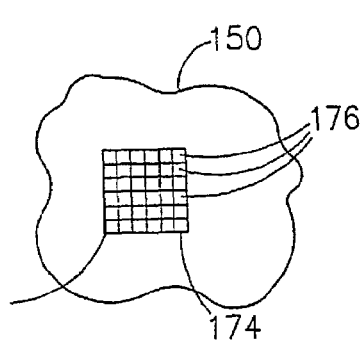
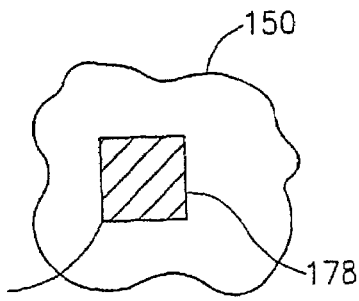
FIG.3D                FIG.3E

DRUG DELIVERY DEVICE

RELATED APPLICATIONS

This application is a U.S. national filing of PCT Application No. PCT/IL00/00832, filed Dec. 13, 2000. This application claims the benefit under 119 (e) of US provisional application Ser. No. 60/137,553, filed Jun. 4, 1999 and is also a continuation-in-part of PCT application No. PCT/IL00/00319, filed Jun. 4, 2000, now U.S. Ser. No. 09/980,908, filed Dec. 4, 2001 the disclosures of which are incorporated herein by reference.

FIELD OF THE INVENTION

The present invention relates to electrically mediated transport of drugs into cardiac tissue and/or into cells of the tissues.

BACKGROUND OF THE INVENTION

Electroporation is a technique used for introducing molecules across a cell membrane and into a cell. In a typical application, an in-vitro cell culture is mixed with a target molecule and a brief electrical field is applied to the mixture. The electrical field causes a transient porosity of the cell membranes, allowing the molecules to enter the cell. U.S. Pat. No. 5,501,662, the disclosure of which is incorporated herein by reference, describes an electroporation system for blood, in which an electric field is applied to a vessel having blood cells mixed with a target gene (or other molecules) and the electric field causes the genes to be transported into the cells. Electroporation is especially useful for large molecules, such as proteins, and for other molecules which do not have a biological mechanism for crossing the cell barrier.

Iontophoresis is a method of transporting drugs into a body tissue, from outside the body tissue, usually from the skin. The drug is provided in a charged form and, when an electric field is applied, the electric field moves the charged drug along the gradient of the field.

PCT publication WO98/15317, the disclosure of which is incorporated herein by reference, describes an implantable drug-eluting tip which uses a cardiac pacing signal to cause charged drug particles to leave a reservoir and be available locally. It is suggested in that publication that the electric field of the pacing signal is sufficient to iontophorese the drug into the heart tissue. Injection of DNA into individual cells is suggested using a similar device, for apply toxins to tumor cells, apparently not in the heart. However, it is not clear whether the fields strengths and durations of a pacing signal are sufficient for electroporation or even iontophoresis for any considerable depth.

U.S. Pat. No. 5,865,787, the disclosure of which is incorporated herein by reference describes a catheter for electroporation or iontophoresis, in which the iontophoresis pulses are applied in conjunction with active pacing.

U.S. Pat. No. 5,387,419, the disclosure of which is incorporated herein by reference, describes a system for controlled release of antiarrhythmic agents.

SUMMARY OF THE INVENTION

One aspect of some exemplary embodiments of the invention relates to using a non-excitatory pulse to control molecule availability at or near excitable tissue, such as the heart, the uterus or the GI tract, which might be activated in an undesirable manner by an applied electric field. The exerted control may include, for example, one or more of causing a molecule to exit a reservoir, iontophoresis of the molecule into tissues, release of the molecule from a circulating reservoir, such as electrically-opened liposomes and/or electroporation of the molecule into individual tissue cells. An optional second non-excitatory pulse may be provided to interact with the first pulse (e.g., to control the tissue) and/or the molecule. In some embodiments of the invention, the molecule availability pulse is excitatory and adverse effects of the pulse are prevented by the second pulse.

As used herein the term "non-excitatory pulse" means an applied electric field which does not induce an additional propagating action potential in the heart (or other relevant excitable tissue), for example due to its frequency, polarity, waveform, duration, amplitude and/or its being applied at a time in the electrical activation cycle when the nearby tissue does not respond to the pulse.

As used herein the term molecule means any type of molecule, including, especially, genetic material, such as DNA and RNA, genetic vectors, such as viruses and plasmids, polypeptides, hormones and small molecule drugs. In addition, the molecules may include ATP, cAMP and/or particles having the molecule adsorbed thereto or located inside a volume of a hollow particle, such as a liposome, which can be transported into the tissue or trapped in a matrix, such as a hydrogel matrix reservoir on the electrode. Exemplary pharmaceuticals include: β-Blockers, anti-cancer drugs, specific antibodies, SERCA, VEGF and Nitro components such as Nitroglycerine. In particular, some molecules may have a systemic toxic effect and/or may damage some organs of the body. In another example, the provided molecule is an antagonist for a different molecule, also present in the body, for example antagonists e.g. Protamine which antagonizes Heparin.

In an exemplary embodiment of the invention, knowledge of what types of pulses will not cause an ectopic excitation and or other arrhythmia, (herein referred to as an arrhythmia) in any particular excitable tissue organ and/or methods for controlling such arrhythmia should they occur are used to apply pulses having larger voltages, currents and/or durations than previously thought possible, to the excitable tissue, for the purpose of transporting drugs. In addition, a variety of waveforms becomes available. Optionally, apparatus designed for non-excitatory pulses is used (e.g., not a pacemaker), making possible various programmable pulse forms and larger amounts of power. However, in some embodiments of the invention, a modified pacemaker/simulator may be used, for example a pacemaker with modified programming, to provide a non-excitatory pulse.

Various types of electrodes may be used. In an exemplary embodiment of the invention the type of electrode used is a point electrode. Alternatively or additionally, a line electrode, a wide area electrode, a vascular electrode which is inserted into a vessel and/or a one- or two-dimensional matrix electrode may be used.

In an exemplary embodiment of the invention, the molecules are provided by the electrode, for example using a drug-eluting electrode of one of various types as known in the art. Alternatively or additionally, the molecule is provided in other ways. For example the molecule is injected systemically or locally or applied using an implanted pump (possibly with output ports at the region to be treated or in a vascular bed thereof or adjacent thereto where the electrical pulse can transport it). Possibly, a decomposing or other matrix having the molecule embedded therein is used to supply the molecule. Alternatively, the molecule is ingested, inhaled or applied topically. In some cases, a plurality of molecules and/or molecule provision methods are used simultaneously in a single patient, for example both systemic and local provision of two different molecules. Optionally, such two or more molecules may interact, for example the local molecule blocking the activity of the systemic one or enhancing it, or vice versa, for example, the systemic molecule blocking the effect of the local molecule outside of the targeted area, where the concentration of the local molecule is lower.

An aspect of some embodiments of the invention relates to an interaction between non-excitatory signals applied and the molecule transport. In some embodiments of the invention, the transport pulse and/or an optionally provided second non-excitatory pulse prevent and/or counteract adverse affects of the transport pulse and/or of the transported molecule, for example by preventing the propagation of undesirable action potentials. In some embodiments of the invention, the transport pulse is applied at a location spatially displaced from the location of the second non-excitatory pulse. In some embodiments of the invention, the adverse effect that is contracted by the second non-excitatory pulse is caused by a non-transport electrical signal, for example an electrical or optical signal used to stimulate cells in or near the excitable tissue to perform angiogenesis.

In an exemplary embodiment of the invention the molecule and the non-excitatory signal cooperate to have a desired, synergistic effect on the excitable tissue, for example the molecule enhancing a contractility increasing effect of the signal or the signal enhancing a contractility increasing effect of the molecule. Alternatively, the signal may be selected to have a minimal (e.g., functional and/or sensory) effect on the excitable tissue.

Various types of molecules may be used in exemplary embodiments of the invention. In some particular embodiments of the invention, non-ionized/charged molecules are used for electrically mediated transport in the excitable tissue. Optionally, the effect of electroporation is achieved by the electric field of the non-excitatory signal momentarily opening pores in the cardiac cell membranes. Alternatively or additionally, dipole charges are formed on the molecules, for transport, by using suitable electric field frequencies. In some embodiments, required field intensities, waveforms or frequencies are provided by virtue of using non-excitatory fields.

An aspect of some exemplary embodiments of the invention relates to a method of treating a dysfunction in an excitable organ. In an exemplary embodiment of the invention, a patient is temporarily connected to a device that electrically transports molecules into excitable tissue. Possibly, the device also performs monitoring functions and/or provides other treatment, such as applying electrical fields that prevent arrhythmia or pacing the excitable tissue.

An aspect of some exemplary embodiments of the invention relates to treating coronary blood vessels or other blood vessels that are near or inside the heart or other excitable tissue, using electrically mediated molecule transport. In an exemplary embodiment of the invention, the timing and/or other parameters of application of electric fields for transporting the molecules are selected to not have a pro-arrhythmic effect on the excitable tissue. In an exemplary embodiment of the invention the molecule transported is one which causes breakdown of clots or other occlusions, one which causes angiogenesis and/or one which prevents stenosis or re-stenosis of the vessel. Alternatively or additionally to using a transport pulse, the therapy may be effected using a non-transport pulse, for example a vessel spasm relaxation pulse. It is noted that pacemaker lead placement usually avoids placing the lead over a coronary vessel, in order to provide better electrical contact with the excitable tissue.

An aspect of some exemplary embodiments of the invention relates to using a non-excitatory pulse generating device to both transport a molecule and detect and/or measure an effect of the molecule, for example an effect on conduction velocity, contractility or action potential propagation. Alternatively or additionally to measuring the effect the device can be used to counteract or block pro-arrhythmic effects of the molecule and/or of the pulse used to transport the molecule. Alternatively or additionally, the device is used to control the type, timing and/or dosage of molecule to be applied.

An aspect of some exemplary embodiments of the invention relates to providing one or more types of molecules at a plurality of locations on the excitatory tissue. In an exemplary embodiment of the invention, the amount of molecule transported and the type of molecule transported at each point is individually controllable. Alternatively or additionally, the application regimen of the molecule may be pre determined. Alternatively, the application regimen may be varied, for example in response to needs of the excitatory tissue or in response to the effect of a previous application. Optionally, a non-excitatory pulse is used to transport the molecule.

An aspect of some exemplary embodiments of the invention relates to synchronizing the transport of a molecule with activity of the excitable tissue, for example the cardiac cycle or cardiac output variations caused by activity, to achieve desirable effects, for example transport effects. Alternatively or additionally, for example for non-cardiac excitable tissue, the synchronization is with on-off (or high-low) activation cycles of the tissue. Three types of synchronization may be distinguished. First is synchronization with the activity of a single cell (or a region) from depolarization to depolarization. The synchronization may be with any part of the electrical cycle, including, for example, an onset of depolarization or a plateau. Second is synchronization with the activity of the excitatory tissue within a cycle. Third is synchronization with longer term activities, such as increase in heart rate due to exercise, uterine contractions due to impeding labor or digestive activity of the GI tract. It is noted that the non-excitatory device can also control the above excitable tissue activities, alternatively or additionally to synchronizing with them. In one example, the molecule is transported at a time when it will have the greatest effect on the heart. In another example, the molecule is transported when travel through the uterine tissue is easiest, for example when the muscles of the uterus are relaxed. Possibly, the non-excitatory pulse is used to extend the refractory time of all or part of the tissue to allow the molecule to travel further in one cycle.

An aspect of some embodiments of the invention relates to releasing a molecule from a circulating reservoir, using a field applied by an electrode associated with a particular blood vessel. Optionally, the particular blood vessel feeds a particular organ or part of an organ to be treated. In an exemplary embodiment of the invention, the electrode is mounted on a stent-like device, on the inside of the blood vessel. Alternatively, the device is mounted outside the blood vessel, for example being a wire implanted electrode. In an exemplary embodiment of the invention, the circulating reservoir comprises a liposome of a type that releases its contents when a sufficiently strong electric field is applied to it. Optionally, the stent also includes a reservoir of a same or different molecule. Alternatively or additionally, the electrode (or a different electrode) also applies a transport field, for example to release a drug from the reservoir or to transport a molecule from the blood flow to the surrounding tissue.

There is thus provided in accordance with an exemplary embodiment of the invention, electrical treatment apparatus for use with an associated molecule source, comprising:

at least one electrode;

a power source for electrifying said at least one electrode; and a controller, which is programmed to activate the power source to selectively electrify said at least one electrode to apply at least one electric field including a transport effect for transporting a molecule in a desired manner and a non-excitatory control effect for controlling the activity of at least a part of a non-cardiac excitable tissue, said programming selected to achieve a desired provision of said molecule into said at least a part of an excitable tissue or associated vasculature, said desired provision being at least assisted by an interaction between the transport effect and the control effect. Optionally, said controller is hardware programmable. Alternatively, said controller is software programmable.

In an exemplary embodiment of the invention, said apparatus comprises a wireless programming input. Alternatively or additionally, said programming comprises programming adapted for said patient. Alternatively or additionally, said programming comprises a setting of at least one operational parameter of said apparatus. Alternatively or additionally, said programming comprises a selection or at least one operational protocol from a set of available protocols in said apparatus. Alternatively or additionally, said controller is operable in a testing mode, in which mode a test treatment of a molecule is provided to the patient and the response of the patient to the test is monitored by said controller. Alternatively or additionally, said apparatus comprises a synchronization connection to a molecule source containing said at least one type of molecule. Optionally, said synchronization connection comprises an informative connection that provides at least one informative signal to said controller, informing of a state of molecule release. Alternatively or additionally, said synchronization connection comprises a control connection that provides at least one control signal from said controller, to control a state of molecule release. Optionally, said molecule source is an electric-field mediated molecule source and wherein said control signal generates an electric field that releases said molecule from said source. Optionally, said synchronization connection is comprised in said at least one electrode used for applying a transport effect. Optionally, said molecule source is integral with said electrode. Alternatively, said molecule source comprises blood dispersed molecules.

In an exemplary embodiment of the invention, said molecule source is integral with said at least one electrode used for applying a transport effect.

In an exemplary embodiment of the invention, said molecule source is integral with said apparatus.

In an exemplary embodiment of the invention, said molecule source is external to said apparatus.

In an exemplary embodiment of the invention, said molecule source comprises a catheter, coupled to said apparatus outside said patient.

In an exemplary embodiment of the invention, said molecule source comprises a source of a plurality of molecule types. Optionally, said controller controls said molecule source to selectively release at least a particular one of said plurality of molecule types.

In an exemplary embodiment of the invention, said apparatus comprises at least one sensor that senses a functional tissue parameter and provides said sensed parameter to said controller. Optionally, said sensor measures a functional tissue parameter relating to the entire excitable tissue. Alternatively or additionally, said sensor measures a functional tissue parameter relating to a portion of the excitable tissue. Alternatively or additionally, said controller analyses said sensed parameter to detect an effect of said molecule on said excitable tissue. Alternatively or additionally, said controller analyses said sensed parameter to detect an activity of the excitable tissue and wherein said controller synchronizes said provision to said sensed activity. Alternatively or additionally, said controller analyses said sensed parameter to detect an effect of said transport field on said excitable tissue. Alternatively or additionally, said controller modifies said at least one electric field to modify said transport effect responsive to said sensed parameter. Alternatively or additionally, said controller modifies said at least one electric field to modify said control effect responsive to said sensed parameter. Alternatively or additionally, said apparatus comprises a watchdog that detects an abnormal effect of said applied fields. Alternatively or additionally, said apparatus comprises a watchdog that detects an abnormal effect of said molecule.

In an exemplary embodiment of the invention, said apparatus comprises a user input for receiving an indication of an effect of said apparatus from said patient. Alternatively or additionally, a single electric field applies both of said transport effect and said control effect. Alternatively, said at least one electric field comprises at least one transport field and at least one control field.

In an exemplary embodiment of the invention, said transport effect and said control effect are provided simultaneously. Alternatively, said transport effect and said control effect are applied sequentially. Alternatively or additionally, said control effect is selectively applied in association with only some of said transport effects.

In an exemplary embodiment of the invention, said apparatus comprises at least one pacing electrode that is controlled by said controller to apply a pacing pulse. Optionally, said at least one pacing electrode is comprised in said at least one electrode.

In an exemplary embodiment of the invention, said transport effect is provided by an excitatory field.

In an exemplary embodiment of the invention, said transport effect is provided by a non-excitatory field. Alternatively or additionally, an output port for generating an output to said patient. Alternatively or additionally, said control effect is selected to prevent an adverse effect of said transport pulse. Alternatively or additionally, said control effect is selected to prevent an adverse effect of said molecule. Alternatively or additionally, said molecule is selected to counteract an adverse effect of said control effect. Alternatively or additionally, said control effect is selected to counteract an adverse effect of said molecule. Alternatively or additionally, said control effect is selected to prepare said tissue for said transport. Alternatively or additionally, said control effect is selected to extend a period of time suitable for provision of said molecule. Alternatively or additionally, said control effect and said molecule are selected to cooperate and effect a desired treatment of said tissue. Alternatively or additionally, said at least one electrode comprises at least one transport electrode for applying a transport effect of said at least one field and at least one control electrode for applying said control effect of said at least one field.

In an exemplary embodiment of the invention, said transport effect and said control effect of said at least one electric field are applied using at least one common electrode of said at least one electrode. Alternatively, said at least one control electrode is spatially displaced from said at least one transport electrode.

In an exemplary embodiment of the invention, said at least one electrode comprises a point electrode. Alternatively or additionally, said at least one electrode comprises a spiral electrode. Alternatively or additionally, said at least one electrode comprises a linear electrode. Alternatively or additionally, said at least one electrode comprises a mesh electrode.

In an exemplary embodiment of the invention, said at least one electrode comprises a plate electrode.

Optionally, said electrode comprises a plurality of independently electrifiable contacts. Optionally, said controllers selectively electrifies said independent contacts to achieve a desired, non-uniform, volumetric dispersion of said molecule, relative to said electrode.

In an exemplary embodiment of the invention, said at least one electrode is connected by wire to said controller.

In an exemplary embodiment of the invention, said at least one electrode is a wireless electrode. Alternatively or additionally, at least one electrode is implantable.

In an exemplary embodiment of the invention, said at least one electrode is mounted on a catheter.

In an exemplary embodiment of the invention, said at least one electrode is an external electrode.

In an exemplary embodiment of the invention, said apparatus is implantable.

In an exemplary embodiment of the invention, said apparatus is comprises in a cylindrical body adapted for implantation inside a blood vessel.

In an exemplary embodiment of the invention, said apparatus is wholly external to the patient. Alternatively or additionally, said transport effect comprises iontophoresis. Alternatively or additionally, said transport effect comprises electroporation.

Optionally, said non-cardiac excitable tissue comprises uterine tissue. Alternatively, said non-cardiac excitable tissue comprises bladder tissue. Alternatively, said non-cardiac excitable tissue comprises digestive tissue. Alternatively, said transport effect comprises releasing a molecule from a circulating reservoir. Optionally, said circulating reservoir comprises liposomes in a blood stream.

In an exemplary embodiment of the invention, said controller coordinates the interaction of a systemic molecule and locally available molecule, to have a synergistic effect. Optionally, said local molecule blocks an effect of said systemic molecule. Alternatively or additionally, said local molecule enhances an effect of said systemic molecule. Alternatively or additionally, said systemic molecule blocks an effect of said local molecule away from said a locality where said local molecule is provided. Alternatively or additionally, said systemic molecule enhances an effect of said local molecule.

There is also provided in accordance with an exemplary embodiment of the invention, electrical treatment apparatus for use with an associated molecule source, comprising:

at least one electrode;

a sensor for sensing a functional state of a non-cardiac tissue;

a power source for electrifying said at least one electrode; and a controller, which is programmed to activate the power source to selectively electrify said at least one electrode to apply at least one electric field including a transport effect for transporting a molecule in a desired manner, synchronized to said sensed functional state.

BRIEF DESCRIPTION OF THE DRAWINGS

FIGS. 3A–3E illustrate various practices of electrode configuration and placement, in accordance with exemplary embodiments of the invention;

DETAILED DESCRIPTION OF EXEMPLARY EMBODIMENTS

General Description of Exemplary Device

Figure 1:
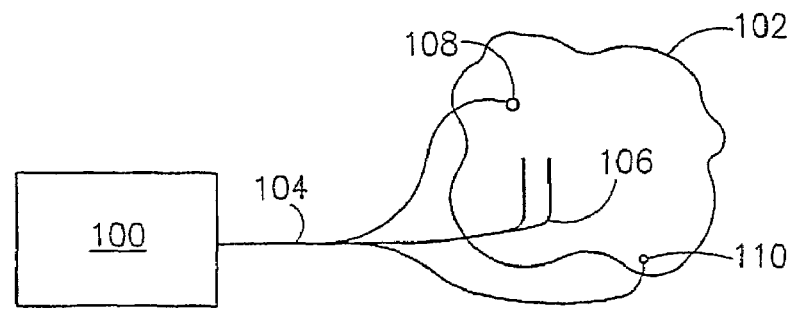
FIG. 1 is a schematic illustration of an excitable tissue connected to a non-excitatory signal providing device, in accordance with an exemplary embodiment of the invention.

FIG. 1 is a schematic illustration of an excitable tissue (e.g., a heart) 102 connected to a non-excitatory signal providing device 100 and showing various optional features of such a connection, in accordance with an exemplary embodiment of the invention. Although much of the following description focuses on the heart, the method sand devices can also be applied to non-cardiac excitable tissues, such as the uterus, the GI tract (e.g. stomach, large and small intestines) or the bladder. Where specific cardiac structures are described, such as coronary vessels and the SA node, corresponding structures in the excitable structures may replace them. Some structures may have an inexact correspondence, for example, a pacemaker location in the uterus or other excitable tissue may move. Alternatively or additionally, there may be no corresponding structure, for example, no AV node in the bladder or multiple corresponding structures, such as the conduction points between sections of the GI tract. In some tissues, a stimulator, rather than a pacemaker, is used.

In an exemplary embodiment of the invention, device 100 is operative to provide non-excitatory signals to the heart and/or otherwise control the heart, as a whole or in portions thereof. In an exemplary embodiment of the invention, some or all of the non-excitatory signals generated by device 100 are used to transport a molecule into the heart tissue or surrounding tissues, in which tissues application of an electrical field might adversely affect the heart. One or more electrode leads 104 provide electricity from device 100 to one or more electrodes 106. A pacer signal electrode 110 may be used to pace the heart, possibly every beat, but optionally not at the same beats as the application of non-excitatory signals. A sensor 108 may be used to provide feedback to device 100 on the effect of the signal and/or the transported molecule.

The ability to use a non-excitatory signal rather than a standard pacing signal (a signal whose task is-to generate a dependable initiation of a cardiac cycle) results in a much wider range of relevant molecules (e.g. heavy, large or less polarized molecules) and treatment possibilities. In particular embodiments of the invention, higher energies and/or longer transport pulses are used. The following table compares a typical pacemaker and a non-excitatory signal providing device in accordance with exemplary embodiments of the invention:

| Characteristic | Pacemaker | Non-excitatory device |
|---|---|---|
| Field basis | Voltage | Current or voltage |
| Amplitude | 0.5–5 Volts, 2 mA | 0.01–40 V, 0.01–150 mA |
| Duration | 0.05–2 ms | 1–1000 ms |
| Effective impedance | 500–1500 ohm | 240–700 ohm, depends on electrode features. |
| Polarity | Usually mono-phasic | Arbitrary |
| Waveform | Usually decaying square pulse | Arbitrary |
| Electrode type | mono- or bi- polar point electrodes | Arbitrary |
| Electrode Location | Limited | Arbitrary |

As a result of the freedom in choosing the field basis, various types of transport effects can be achieved, for example voltage based effects, current density based effects and/or charge based effects.

The available current and voltage amplitudes make it easier to transport large molecules, provide deep tissue iontophoresis or even electroporation. The available durations complement the available amplitudes levels by allowing a much longer transport time. The use of large electrodes and mesh electrodes, for example as described below, allows the local treatment of many locations in the heart and/or the treatment or large areas of the heart, which is not possible using a standard pacing lead. Also, this can lower the impedance of the electrode.

Various suitable structures and electrical fields are described in a series of PCT applications filed by Impulse Dynamics (previously NTC), now U.S. patent application Ser. Nos. 09/254,900, 09/254,902, 09/254,993 and 09/254,994, the disclosures of which are incorporated herein by reference.

Exemplary Pulse Properties

It is suggested in U.S. Pat. No. 5,865,787, an exemplary range for iontophoresis is between 200 Hz and 10 MHz, for example between 2 and 15 kHz. However, in some embodiments, DC waveforms are used. Wave from generators are described in U.S. patent application Ser. Nos. 08/110,109 and 07/957,209, both abandoned, the disclosures of which are incorporated herein by reference. With regard to electroporation, frequencies between 0.017 and 10 Hz are suggested. Voltages between 100 and 10,000 volts are suggested, with electrodes between 0.5 and 10 cm apart. Pulse durations are suggested between 1 microsecond and 1 second, more typically 100 msec. It is noted, however, that by providing a non-excitatory field to counteract adverse affects, a wider range of fields and field parameters is available, so the above should be taken as only exemplary field parameters.

Additionally, exemplary pulses and/or apparatus which may be useful can be found in U.S. patent application Ser. No. 08/129,252, now abandoned, U.S. Pat. Nos. 5,634,899, 5,286,254, 5,087,243, 5,458,568, 5,282,785 and U.S. Pat. No. 5,236,413, the disclosures of which are incorporated herein by reference.

In general, the applied transport pulses may have a net zero charge flow or they may have a non-zero net charge flow, which may need to be compensated by an after-transport charge zeroing current, that balances out the charge emitted by the electrode.

In some embodiments of the invention, the non-excitatory field is combined with an excitatory, portion, for example for pacing.

Exemplary Molecules

As will be appreciated from the more detailed description below, a wide variety of molecules may be used for practicing various embodiments of the present invention For convenience, the following classification of types of relevant molecules is provided, but it is not to be construed as limiting the range of applicable materials. Many molecules are known to be provided and/or transported using an electric filed, for example in the field of patch iontophoresis. It should be noted that a single molecule can belong to several of the classifications described below. Also, the type of transport method used may affect the behavior of the molecule and, hence, its classification.

(a) Duration of Effect. Some molecules have an extended effect, possibly even a permanent effect. In some cases, the duration is long enough that the heart adapts ("modeling"), whereby a desired effect of the molecule can be achieved. Other molecules have a transient effect, possibly as short as a single or a small number of beats. Exemplary molecules include Esmolol with a duration of ~10 minutes and Adenosine with a duration of tens of seconds. These molecules also have a rapid response.

(b) Rapidity of Response. A differentiation should be made between effect on the heart as a whole and effect on individual cells. Some molecules have an immediate effect on the heart, for example within a single or a few cardiac cycles, for example Adenosine in seconds, and Esmolol in minutes. Others, for example genes for providing ionic channels and/or for changing conduction velocity, may have their main effect only after a considerable period of time.

(c) Size of Molecules. Molecules come in all size ranges. One important effect of the molecule size is its ease of entry into a living cell. Another is the ease of transport by electrophoresis. An example of a small molecule is nitroglycerin. An example of a large molecule is a DNA antisense molecule.

(d) Polarization. The degree of polarization of a molecule affects not only its solubility and ability to enter cells but also the type of electric field which can most efficiently transport it. Using stronger fields, various pulse envelopes, various frequencies and/or longer pulse durations supports the transport of molecules that are otherwise difficult to transport.

(e) Existence of Hydrophobic and Hydrophilic Moieties. Such moieties affect the behavior of a molecule during transport and during entry into a cell.

(f) Ability to Self Transport into Cells. Some molecules, such as viruses and liposomes can more readily insert themselves into cells than raw DNA.

(g) Type of Adverse Effect on Cell. Some molecules adversely affect some types of cardiac cells, for example killing or disabling them. Other molecules only affect some functions of the cell, for example their electrical activity, without affecting other functions, such as their basic metabolism or life expectancy. In a particular example, ion channels (provided directly or genes for ion channels provided) can modulate electrical activity and/or cause metabolic changes. This can result in death for some cells and in a cure for other cells. Specifically, increased population of membrane potassium channels can shorten action potential, lower membrane potential and/or change the refractory periods of a cell.

(h) Drug Combinations. Instead of transporting only a single molecule, multiple molecules may be transported, possibly through different means. If the effect of the two molecules together is different from that of the individual molecules, in type and/or amplitude, better targeting of portions of the heart can be achieved, for example by providing the two molecules so they only intersect in one area of the heart.

(i) Drug vs. Non-Drugs. Although many of the suitable molecules are drugs, other molecules may also find use, for example signaling molecules, such as hormones, cytokines and/or paracrinic signals/hormones, both natural and synthetic. Additionally or alternatively, various types of genetic-related molecules may be used. Alternatively or additionally, membrane proteins, such as voltage gated channels may be used. Alternatively or additionally, structural proteins, such as actin, may be used. Alternatively or additionally, housekeeping proteins, such as Ubiquitin, may be used. Alternatively or additionally, solutes, such as glucose, cAMP, AMP, ADP, ATP and metal salts may be used.

(j) Protection of Molecules. Although drugs and other molecules may be transported in a raw state, in some cases, the drugs may be protected against interaction with the blood, extra-cellular liquids, cell membranes and/or other materials which intervene between the drug source and its target. Such protection may take the form of encapsulation, for example in liposomes or incorporation, for example by caging into polyester gels.

(k) Association for Transport. In some cases, the molecules may be associated with other materials, to assist in transport or in the entry into cells and/or nucleus of cells. In one example, a drug may be adsorbed to a pellet, which pellet is more easily transported by the fields. In another example, the molecule is incorporated in a virus.

(l) Genetic Material. As will be described below, a particular desirable class of molecules is gene-related molecules, such as DNA, RNA, mRNA, etc., anti-sense molecules and proteins that affect transcription.

(m) Microorganisms. In some cases, it may be desirable to insert complete or semi-complete microorganisms or cell components into living cells, for example mitochondria, viruses or plasmids.

As can be appreciated, the molecule may interact in a beneficial, neutral or adverse manner with one or more of the transport method, the provision method, the cardiac sensitivity (e.g., to electrical fields and certain molecules) and/or the instantaneous activity of the heart. These effects (if negative) may be overcome or enhanced, in some embodiments of the invention, by suitable varying of the transport method and of the molecule properties, for example as classified above.

Gene Therapy

In an exemplary embodiment of the invention, electroporation techniques are used to provide gene therapy to the heart. In gene therapy, genetic material or a carrier thereof, such as plasmids, artificial chromosomes or viruses particles are provided into a cell. Examples of suitable genetic material include, anti-sense DNA, RNA and poly-peptides to block the expression of genes which have an undesirable effect. In another example, tagging material is inserted to the cell, to serve as a trigger for more complex activity. In one example, regeneration of particular cells is achieved by tagging cells using a genetic marker. A second therapy is applied systemically but is only taken up or only triggers the tagged cells. The provided genetic material may be used for various purposes, including, for example modifying the cell genotype, curing a genetic defect or a viral disease, causing a cell to differentiate in a desired manner or changing the function of a cell, such as changing the conduction velocity, action potential profile and/or leakage current characteristics of the cell.

In a paper in Nature 1999, Sept. 23; 401 (6751) pp390–394, the disclosure of which is incorporated herein by reference, Mulligan R C, et al. describe a mechanism for targeting stem cells to where they are required in the body. It is believed such stem cells are targeted by a localized inflammation process, which process may be artificially and locally induced using a suitable molecule in accordance with an exemplary embodiment of the invention.

A particular aspect of some types of genetic therapy (and also of some drugs) is that the cell's behavior is modified. As a result, the cell may affect other, neighboring, cells, for example by creating copies of the genetic material (e.g., virus) or by extruding hormones and other cellular-communication chemicals.

In another example, tissues near clogged arteries are genetically modified, for example with a plasmid, to generate an anti-coagulant, a clot dissolver or a vascular dilator. These materials are optionally provided locally in a therapeutic concentration, so that they are diluted in the general blood stream. Alternatively or additionally, these materials only reach active concentrations and/or required activity times if the blood volume flow is reduced relative to normal blood vessels.

In another example, the heart as a whole is affected by the treatment of a small set of cells. For example, cells can be treated to include more calcium or sodium channels, thereby causing the treated cells to form a pacing loci. Depending on the type of treatment (e.g., plasmids, viruses or channel proteins), the effect may vary in duration, thereby allowing different pacing locations to be chosen.

Device Components

Apparatus suitable for performing (or being modified to perform) the function of device 100 of generating non-excitatory signals are described, for example in PCT application PCT/IL97/00012, and PCT publications WO 99/03533 and WO00/53257, the disclosure of which is incorporated herein by reference.

Figure 2:
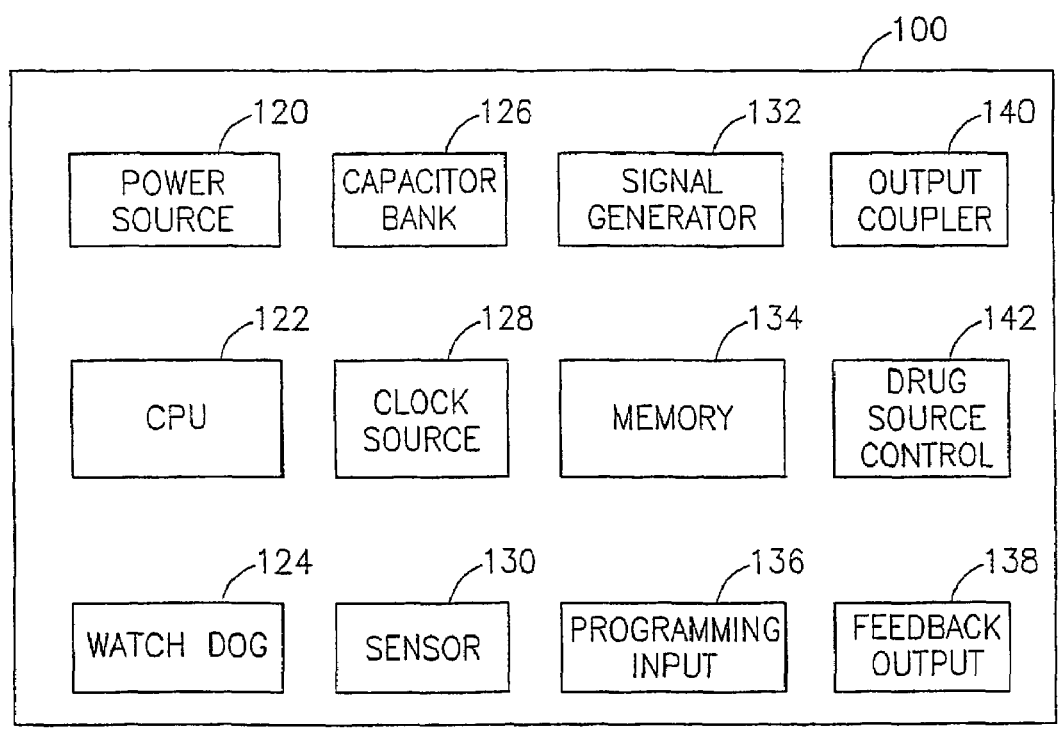
FIG. 2 is a schematic box diagram of internal sub-components of the device of FIG. 1, in accordance with an exemplary embodiment of the invention.

FIG. 2 is a box diagram of exemplary sub-components of an exemplary device 100, in accordance with an exemplary embodiment of the invention. Although many possible sub-components are shown, some embodiments do not require all of the sub components, for example, some embodiments do not include watchdogs or programming input. For clarity, connecting lines between the sub-components are not shown.

The non-excitatory signals are generated by a signal generator 132 and outputted to the electrodes via an output coupler 140. The power for driving the output signals maybe provided directly from a power sources 120, or, more typically, using a capacitor bank 126 to accumulate power. In a device that includes a pacing feature, some or all of these elements may be optionally shared between the pacemaker and the non-excitatory signal pathways.

A CPU 122 is optionally provided to control device 100. A clock source 128 may be used to maintain an internal clock.

In an exemplary embodiment of the invention, CPU 122 uses a state-machine model of the heart to assess if the heart is operating as expected and/or to determine the possible timing of non-excitatory pulses, especially for drug transport. Alternatively or additionally, other state-machine models may be used. Alternatively, a non-state machine model is used. Various types of models are described in "Design of Cardiac Pacemakers,", ed. John G. Webster, 1995, by the Institute of Electrical and Electronics Engineers, Inc., New York, N.Y., the disclosure of which is incorporated herein by reference.

In an exemplary embodiment of the invention, CPU 122 utilizes sensor data from a sensor input 130, in determine application parameters. Although only a single sensor is shown, in some devices, more than one sensor is used. Optionally, device 100 includes a memory 134 for storing programming instructions, applied sequences and/or statistics and/or full data of the response of the heart at various times.

In an exemplary embodiment of the invention, a programming input 136, preferably wireless, but optionally wired, is provided to allow programming the device, for example using RF, ultrasound or magnets. Alternatively or additionally, a feedback output 138 is provided for presenting information from device 100 to an external programmer or user. A particular use of the programming features is to assist in setting and modifying treatment regimes and/or adjusting existing regimes to take into account observations by a treating physician. Another use is allowing a patient to be treated at home and report by remote means, such as a telephone, the actual treatment and/or its effect. The setting of treatment parameters may also be by remote means. Another possible use of output 138 (and programming input 136) is for receiving feedback from the patient.

In an exemplary embodiment of the invention, the user of the device can activate device 100, using a handheld remote controller, which may optionally also beam energy, for example using RF radiation. Alternatively or additionally, the remote control may include activation logic for the device. A single remote controller can activate multiple devices, for example one or more of, a non-excitatory signal controller, a pacemaker, a drug targeting electric field(e.g., device 100) and a drug reservoir, to achieve a desired treatment effect. In an exemplary embodiment of the invention, the user activates device 100 in response to pain, for example, to release blood vessel dilating molecules in response to angina pectoris or to inhibit premature uterine contractions.

In an exemplary embodiment of the invention, device 100 includes one or more watchdogs 124. Two types of watchdogs may be utilized in an exemplary embodiment of the invention. A first type of watchdog watches over the device itself, to assure that it is working within the operational parameters defined for it. For example, two processors run concurrently, and if one is not responding, the other one generates an alert. A second type of watchdog watches over the heart, to assure that the heart does not, as a result of the treatment, exceed operational and/or functional parameters defined for the heart's activity. In one example, the watchdog checks to see if the heart is acting differently after the transport pulse. Alternatively or additionally, the watchdog searches for particular tattletale signals of damage more likely to be caused by the treatment, for example, a certain type of arrhythmia in an pro-arrhythmic drug treatment or VT caused by the transport pulse. The damage and/or danger may be immediate, for example the detection of an injury current or of VT. Alternatively or additionally, the damage or danger detected may be longer term, for example, if the treatment causes a forced relaxation of part of the heart, which relaxation may cause hypertrophy or an aneurysm. A separate feedback loop may be provided to detect if the treatment is having a desired effect, for example a desired remodeling of cardiac tissue. Optionally, the watchdog is implemented as a separate processor and/or sensor. Alternatively, the watchdog comprises separate software.

The output of the watchdogs may include, for example, output to the patient, to a remote service center and/or may include a changing in the device parameters, for example to stop or modify the treatment or to provide symptom countering treatment, such as blocking of undesirable action potentials of transport of a different molecule.

In an exemplary embodiment of the invention, device 100 is implantable. Thus, device 100 is optionally encased in a small capsule, to be implanted in the chest or the stomach of the patient. Device 100 may be integrated with a pacemaker or it may be a separate entity.

Alternatively, device 100 is external. The electrodes are optionally internal, optionally reaching the heart either via a catheter inserted in the blood stream or via a hole in the skin, for example to effect a near-by vessel or part of the heart. The molecules may be provided using the same catheter or in a tube alongside the electrodes. Alternatively, other molecule provision methods, for example as described below, may be used.

Alternatively, the electrodes may be external to the body, for example as used in some external pacemakers. Various electrode schemes may be used, including, two large, two small, one large and many small, an array, electrode(s) in lungs and/or electrode(s) in esophagus. Optionally, the electrification of the electrodes matches the heart's position and/or global or local refractory state.

In an exemplary embodiment of the invention, an external device is used for a short-term treatment, such as for gene therapy, for recovery from surgery or for recovery from a serious arrhythmia or acute ischemic event. Alternatively, an implanted device may be used for medium term treatment. Alternatively, a previously implanted device may be reprogrammed to apply a non-excitatory pulse as described herein. In some embodiments of the invention, only the electrodes are implanted and wireless. The rest of the device is external and is used to power and drive the electrodes, for example using RF radiation.

Alternatively or additionally, the functionality described herein may be integrated with a different device, for example, a stent. In one exemplary application, a stent applies non-excitatory pulses to transport an anti-re-occlusion drug into the blood vessel walls. The drug may be provided in many ways, including, for example, from the blood stream, from a reservoir of the stent or from a catheter.

In an exemplary embodiment of the invention, the device is a dedicated device. Alternatively, however, some or all of the functionality may be achieved using a modified pacemaker, in which substantially only the programming and/or electrodes are modified. The suitability of existing pacemaker circuitry and/or power supplies may depend, for example, on the effect desired (e.g., electroporation or iontophoresis) and on the molecule size, polarity and/or other properties, such as protective enclosure.

In one embodiment of the invention, device 100 comprises a kit of two devices, one for providing the electrical fields and one for providing the molecule. Either or both of the devices may be implantable, external partially implanted or transvascular. A drug source controller 142 is optionally provided in device 100 to control the provision of molecules. Alternatively, a third device, such as an external or implanted controller (not shown), synchronizes the operation of the two devices.

Alternatively, one device is used for transporting the molecule and another device is used for pacing or non-excitatory control (molecule provision can be by either of the devices or using a separate device). In this embodiment, the other device can be used to counteract adverse effects of the transport and/or the applied molecules. In an exemplary embodiment of the invention, the two devices can communicate, for example using a wireless link, such as an ultrasonic link or a wired link, such as a fiber optic cable.

Electrodes

FIGS. 3A–3E illustrate various practices of electrode configuration and placement, in accordance with exemplary embodiments of the invention. The type of electrode can be an important factor in determining the strength and distribution of the electric field. By changing the type and shape of the electrode, different types of transport maybe effected. In addition, the depth of penetration and spatial distribution of the molecule into the cardiac tissue is affected, not only by the electrification of the electrode but also by the shape of the electrode. The placement of the electrodes determines which part of the heart is affected and, together with a suitable selection of electrode type and shape, allows localized treatment of specific portions of the heart, such as the SA node. In addition, certain multi-electrode types, such as mesh electrodes or electrode arrays, provide a greater temporal and spatial control of the electric field Although the electrodes may be placed anywhere on the heart (e.g., inside the muscle, inside blood vessels or inside the heart), in some embodiments of the invention, the electrodes are placed at an arterial entrance, an area of infraction, at an ectopy site, near a block or an AV node, inside or at a border of a scar and/or at the nervous plexus.

FIG. 3A illustrates the placement of a point electrode 160 on a cardiac segment 150. In a point electrode the strongest part of the electric field is in a close proximity to the electrode, indicated by a dotted line 162. If a bi-polar electrode is used, the localization of the field is even greater, being mainly between the two electrodes. Alternatively, a common return electrode may be used, for example a casing of device 100 or a second electrode attached to a substantially remote portion of the heart. Various tip shapes may be provided, for example, solid or meshwork balls, multi-fingered tips, spirals and/or a barb.

FIG. 3B illustrates the placement of a line electrode 164 on cardiac segment 150. A simplest type of line electrode has contacts along its length, as shown. Alternatively, a line electrode may comprise a plurality of spaced apart point electrodes which may be electrified in parallel or possibly in various orders, as a linear array. A region 166 affected by electrode 166 is substantially larger than that of a point electrode. This can be used to apply a molecule to a larger portion of the heart or even to create a "fence" by applying a desensitizing drug along the electrode. In some embodiments of the invention, such a line electrode is curved.

FIG. 3C illustrates the deployment of a pair of line electrodes 168 and 170. The affected area (in which there is a significant electric field) is marked by a dotted line as 172. The two electrodes may be electrified with a same polarity or with opposing polarities. Additionally, if one or both lines comprises a linear array of point electrodes, these point electrodes may be scanned in synchrony or not. The size and shape of affected area 172 is dependent on the type of electrification. For example, if the two electrodes are electrified with different voltages, there will typically be very small field outside of the electrodes, which may, in some embodiments, prevent the molecules from being transported outside of the electrified area.

FIG. 3D illustrates a mesh electrode 174 having a plurality of vertexes 176. In one embodiment, the entire mesh is electrified as a single element. In another embodiment, only the vertexes (or other segregated section of the mesh) are electrified (e.g., an array). In another embodiment, at least some of the vertexes can be selectively electrified. One advantage of selectively electrifying mesh (or line) vertexes in an electrode array is that there is finer control over the shape, location and intensity of the field and this control can be exerted in real-time, without requiring movement of the electrodes. One use of such control is for modifying the transport field to effect a certain transport effect, for example as defined below, for adapting a pre-conceived electrification protocol to a particular heart and/or situation and/or to match the actual or expected propagation of the molecule in the heart. Alternatively or additionally, such control may be used to match the propagation of electrical waves in the heart or to match changes in the contractile state of cardiac muscle. In one embodiment, these states are estimated using a model. Alternatively, these states may be measured using suitable sensors.

In a particular embodiment of the invention, the molecule is provided at a mesh electrode. Optionally, the mesh electrode is electrified in a manner which distributes the molecules in a desired manner, for example electrifying pairs of vertexes in the mesh such that each such pair defines a different transport vector, for example all the electrification pairs sharing a common electrode. Alternatively or additionally, the timing, amplitude and/or other electrification parameters are different for each electrode pair, taking into account, for example the different average activation times of the heart and/or the instantaneous different activation time. Such an instantaneous activation time may be detected, for example, using the mesh electrodes as sensors or by providing dedicated sensors.

FIG. 3E illustrates the use of a plate electrode 178. Such a plate may have apertures (not shown) formed in it, so it is not completely solid. In an exemplary embodiment of the invention, electrode 178 may serve as a reservoir, for example including a suitable matrix encapsulating the molecule, or having an inner volume, for example enclosed by an electrically permeable membrane.

The electrode configurations of FIGS. 3A–3E may be applied outside of the heart muscle, inside the heart muscle or on the inside of the heart. Additionally, when using electrode pairs, one may be inside the heart tissue and one outside the heart tissue. Alternatively or additionally, at least one of the electrodes may be floating inside the heart. In some embodiments, the electrodes are coated with a layer of material to retard clotting.

Molecule Source

The molecules may be provided in various manners; for example as described below. Two main types of provision should be differentiated, localized provision and systemic provision. In localized provision methods, the concentration of the supplied molecule is significant only at or about the treatment area. One possible advantage of this type of provision is that effects on other body portions are reduced. Another possible advantage is that a smaller amount of molecule may be used. Another possible advantage is that a higher concentration of molecule can be realized at the treatment zone.

In systemic provision methods, one possible advantage is that there is no need to provide a molecule at precise temporal and/or spatial coordinates. Rather, the electrical transport effect is used to locally increase the effectiveness of the molecule, by transporting it to the tissue to be affected, for example from the blood stream.

Figure 4:
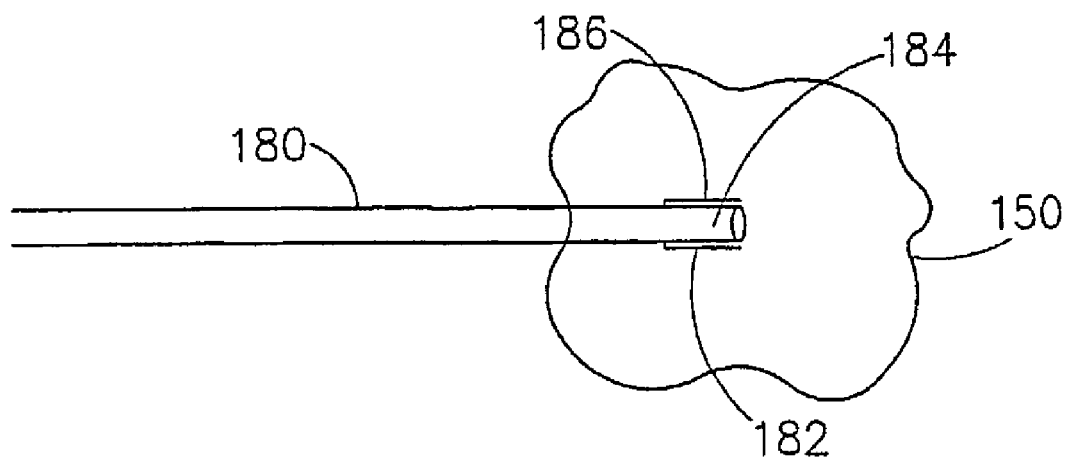
FIG. 4 is a schematic illustration of a molecule provision apparatus, in accordance with an exemplary embodiment of the invention.

One method of localized molecule provision is in association with one of the electrodes of the device 100. FIG. 4 is a schematic illustration of a molecule provision apparatus, in accordance with an exemplary embodiment of the invention. A lead 180 has at its end an electrode 182, for applying a non-excitatory electric field to a heart segment 150 and a drug-eluting portion 184. In one embodiment, lead 180 is a hollow tube which caries the molecule from a reservoir inside device 100 (not shown). Such a reservoir is amenable to replenishment, for example as known in the art of replenishing implanted medication pumps. Alternatively, lead 180 itself may serve as a reservoir. In one example, lead 180 is a hollow tube which caries the molecule from a reservoir inside device 100 (not shown). Such a reservoir is more amenable for replenishment, for example as known in the art of replenishing implanted medication pumps. Alternatively, lead 180 itself may serve as a reservoir. In one example, lead 180 is hollow and filled with a liquid medicament. In another example, the medicament is solid and is dissolved by body fluids only at the distal end thereof. In another example, a molecule is constrained in a gel matrix inserted inside lead 180. In some embodiments, an electric field is used to advance the molecules along the lead, for example as described in U.S. Pat. No. 5,865,787. In general, a reservoir may be useful where local provision of a molecule is desirable.

Alternatively or additionally, tip 184 may be porous, allowing the molecules to slowly diffuse out.

In an exemplary embodiment of the invention, an electric field applied by electrode 182 is used to elute the molecule from tip 184. Tip 184 maybe, for example, between electrode 182 and the heart, on an opposite side of the heart from the electrode or side by side with it. Additionally, one or both of electrode 182 and tip 184 may be inserted into the cardiac tissue. A same field may be used for eluting and for transport or a different field may be used. Alternatively or additionally, one or more additional electrodes 184 may be used to assist in the eluting. PCT publication WO 98/15317 describes a limited range of possibilities for selectively eluting molecules from a drug-eluting tip. In exemplary embodiments of the instant invention, the freedom of electrode shape, charge polarity, charge amplitude, charge duration, charge location and waveform allow a much wider range of methods to be practiced. As a result, it is possible to selectively elute one of several molecules which are stored in one or more reservoirs about tip 184. In one example, the polarity of the field determines the polarity of molecule eluted. In another example, the field amplitude determines what size molecule is transported and/or opens pores in a barrier material between the molecule reservoir and the outside of the tip. In another example, molecules with dipole charges may be selected by applying a suitable elution frequency. Alternatively, non-electrical transport methods are used to free the molecules, for example, operating pumps or openings in a reservoir.

Figure 5:
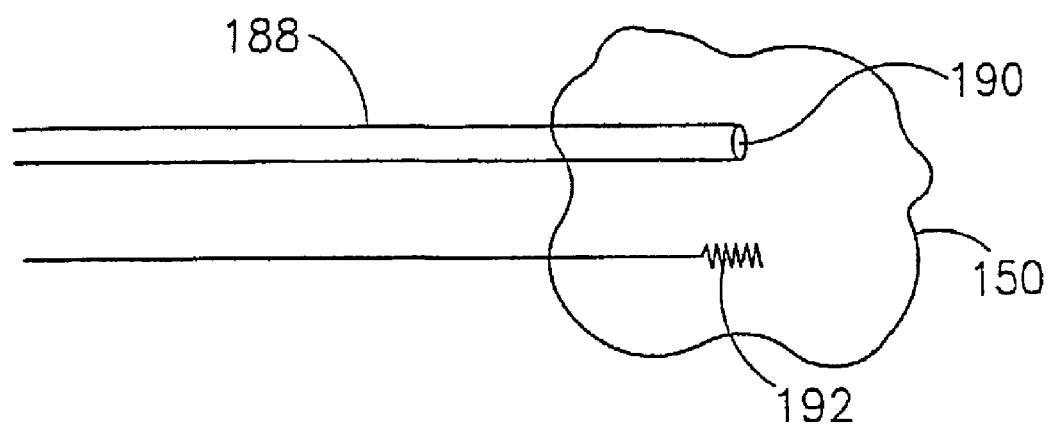
FIG. 5 is a schematic showing of a catheter-based molecule provision configuration, in accordance with an exemplary embodiment of the invention.

FIG. 5 is a schematic showing of a catheter-based molecule provision configuration, in accordance with an exemplary embodiment of the invention. A catheter 188 is used to provide the desired molecule from outside of the body, to its tip in a vicinity of electrode 192. Alternatively or additionally, the catheter may be drug eluting over a portion of its length. The molecules may be provided at a location from which they are advanced away from the electrode. Alternatively, the molecules may be attracted towards the electrode. Alternatively or additionally, the electrodes may be electrified to prevent the advance of the molecules in an undesired direction.

Alternatively to providing the molecules locally to electrode 192, the molecules may be provided into a vascular bed of the area adjacent electrode 192, for example into a main coronary artery. In an exemplary embodiment of the invention, the application of the electrical field is timed to match the arrival of the molecule bolus. Alternatively or additionally, the provision of the molecule is over an extended period.

In an exemplary embodiment of the invention, the application of the electrical field (and/or localized molecule provision) is timed to when blood flow is slow, to avoid dissipation of the molecule. Alternatively or additionally, tip 190 may block the flow of blood, optionally temporarily, for example using an inflatable balloon collar. Alternatively, a double collar catheter having two spaced apart collars and a hollow lumen, may be used to block flow to only a portion of a vessel, while providing a molecule to the blocked off area and allowing the flow of blood to by-pass through the lumen of the catheter. Alternatively, tip 190 may be pressed against the tissue to be treated, optionally in the direction of the field, so that the molecule can only advance through the tissue and not into the blood flow. Alternatively or additionally, a local electric field may be applied to reduce or increase blood flow, for example by relaxing or contracting the blood vessel muscles. Such relaxation may also assist in the penetration of the molecule through or into the vessel walls.

The timing of the application of the electric field may take into account a model of propagating of blood in a heart in general and/or in the particular treated heart. Such a model may be derived, for example, from radiological studies of the propagation of radio-opaque dyes in the coronary vessels.

Alternatively or additionally, tip 190 injects the molecule directly into tissue. Such injection may be achieved by providing a sharp tip at tip 190 or by the catheter exiting the blood flow or being provided not through the vascular system, for example through tissue or along body lumens such as the lungs or the GI tract.

Electrode 192 may be implanted by a catheter that may also be provided from outside the body. In one exemplary embodiment of the invention, the catheter and electrode are combine in a single invasive device. This device may be inserted into the body and brought to a desired treatment location, for example the apex of the heart. Then, a molecule is eluted (optionally at the electrode) and an electric field applied to treat the region. A bipolar electrode may be used or the second electrode may be provided outside the body, or inside, for example using a second catheter, between which catheters a transport electric field and/or a heart control electric field are applied. Optionally, the tip of the catheter inside the body includes a grasping device for attaching to a portion of a tissue adjacent the treatment area. Such a catheter optionally includes a sensor for sensing local activity of the heart or is controlled (e.g., field application and/or molecule provision) using an external sensor, such as a 12-lead EKG sensor. Possibly, the catheter elutes a molecule along a portion of its length, allowing, for example, a length of a coronary vessel to be treated. Different molecules or concentrations of molecules may be eluted at different points along the catheter.

The combined catheter-electrode may be provided via the vascular system. Alternatively, an endoscopic or throactoscopic approach may be used. Such a device may be used for relatively chronic treatment, for example one treatment a week after a coronary event. Alternatively, the device may be used for acute treatment, for example to provide a drug to a portion of the heart during cardiac surgery.

Another method of localized provision of a molecule is by injecting it into the heart using a syringe (from outside the body). Optionally, the entry and retraction of the syringe are controlled using a spring-loaded device, so that contact with the heart is during a non-excitable portion of the cardiac cycle, to prevent arrhythmia.

Many systemic molecule application methods are known and may be used with various embodiments of the invention, including drip-feeding into a vein, catheterization into the right atrium, ingestion, inhalation and intra-vascular or intra-muscular injection.

In an exemplary embodiment of the invention, device 100 includes a data input port for indicating when a drug is injected or otherwise provided into the user, so that the application of the non-excitatory signal can be timed to when the drug (or other molecule) is available at the electrodes. Such an input may be provided for example using a magnet or an RF field.

Transport and Selectivity

The non-excitatory pulse used for transporting the molecule may be a separate pulse from that used for a non-excitatory based treatment, it may be a combined transport-treatment pulse or it may be a same pulse which has both a treatment effect and a transport effect. Possibly, a molecule may be selected or adapted for treatment by it matching available pulse forms or pulses which have a known therapeutic effect.

As described above, the transport mechanism may be that of removing the molecule from a reservoir using an electric field. Thereafter, the molecule can diffuse into the adjacent tissue (or wherever the blood caries it) or an active transport (e.g., an electric field) into adjacent tissue may be used.

Two types of transport can be differentiated, transport into tissue and transport into cells. Transport into tissue can be, for example, iontophoresis. Alternatively, uncharged molecules, for example those with a dipole charge may be used. Alternatively or additionally, the application of the electric field may make the tissue more porous to the diffusion of the molecule.

In one exemplary embodiment, of the invention two or more of the above transport mechanisms are used together. For example, electroporation into the cardiac cells themselves may be used instead of or in addition to iontophoresis, for example, iontophoresis to advance a drug into the cardiac tissue and then electroporation to insert the drug into the cells. The two mechanisms may optionally be applied in separate cardiac cycles.

Various types of selectivity may be achieved, besides selectivity of the transported molecule, described above. In one example, the iontophoresis of a molecule is affected by the tissue through which the molecule travels. In another example, the field strength used for electroporation is selected to affect only certain types of tissue, for example based on their taxonomy (muscle vs. nerve cells) or based on their health.

It should be noted that the molecules may be transported during any part of the cardiac cycle, to take advantage of (or avoid) particular electrochemical and/or physiological conditions. Alternatively or additionally, a molecule may be selectively provided and/or transported so that it is available at the cells when their channels in the cell membrane open as part of the cardiac cycle. Such a molecule may be transported through the channel or it may be used to block the channel or to maintain it open for longer periods. Alternatively or additionally, a transport pulse may be provided to maintain the channels open for longer periods (or close them), for example to provide a desirable biochemical state in the cell with which the molecule can interact or to allow the molecule to enter through the open channel. The exact electrification parameters may need to be determined for a particular patient, tissue type and/or tissue health state.

It should be appreciated that diffusion of drugs and other molecules in the heart may be enhanced by diffusion between cardiac muscle cell groups, in which groups, the cell-ends are fused together. Alternatively or additionally, the transport may be affected by the fiber direction and/or other macro-cellular structures. These effects can be used to selectively diffuse molecules along a direction. Also, these variation in tissue characteristics may affect a desired electric field to be used for transport between and/or into cells. In an exemplary application, an electric field is used to transport a molecule into endocardial trabecula, while they are being filled. Then when they contract and force blood into the surrounding cardiac tissue, the transport is enhanced. Optionally, a second electric field is timed to the contraction.

Alternatively or additionally, the transport of molecules may take into account the variations in muscle tone over the cardiac cycle. Thus, an increased field may be required while the muscle is tense. Alternatively, the transport is selectively applied while the muscle is relaxed, to increase the depth of penetration of the molecule. Alternatively, the transport is applied when the muscle is tense, to assure a shallower penetration, In an exemplary embodiment of the invention, a multi-beat transport scheme is used, in which a molecule is transported to an area to be treated by a transport process which is longer than one beat. In one example, a molecule may be transported 1 mm each heart beat, for a total of five beats, to achieve a penetration depth of 5 mm.

Type of Control

The control exerted on the heart using the molecules and/or a non-excitatory electric field can be of various types. Three particular types of control which may be desirously achieved are global control, local control and global control using local interactions.

In an example of global control, a gene may be provided to the entire heart, to correct a disease causing mutation in a particular patient.

In an example of local control, a drug may be provided to an infracted area to promote healing or prevent further damage.

In an example of global control mediated by local interactions, control of the SA node, of the AV node or of a particular conduction pathway may be used to affect the activation of the heart as a whole.

It should be noted that the fastest action potential conduction in the heart is near the surface of the inside of the ventricles. Controlling the conduction velocity in this area provides an opportunity to affect the activation of large sections of the heart. This area is also somewhat more accessible to some electrically based transport techniques, since a drug can be applied directly to the inside of the heart.

As described above, with reference to molecule provision, the type of interaction of the molecule with the heart may depend on cellular or on cardiac processes, for example, a drug may be provided to coincide with the high levels of availability of free calcium. Alternatively, a molecule may be provided so that it is available over a longer period of time, such as an entire beat or several heart beats. Exemplary periods of time for a molecule to be available are 0.1, 1, 10, 100 or 1000 seconds, e.g., in some cases substantially permanently. The duration of the molecule effect, which may be divorced for the duration of availability may be, for example, 1, 10, 100 or 100 seconds, e.g., in some cases substantially permanent. Some types of long cardiac-related cycles include the circadian rhythm exercise-rest cycles and the application of molecules to the heart to permanently change the shape and/or activation of the heart. In an exemplary application, electric fields are used to stimulate angiogenesis and a stimulating molecule, such as VEGF is also provided to enhance the angiogenesis effect. The molecule (and transport field) may be applied every beat or only every few beats. In some embodiments of the invention, a single transport event continues over several beats or has the duration of several beats, for example with the local tissue being desensitized so it does not contract.

In an exemplary embodiment of the invention, selective molecule providing is used to control the heart locally and/or for temporally short periods, such as seconds or tens of seconds. This effect is achieved by selectively transporting fast acting drugs to target tissues, in short times and without substantially providing the drugs to nearby tissues. Alternatively or additionally, this affect is achieved by electrically (or using suitable eluted pharmaceuticals) de-sensitizing neighboring tissue from responding to the drugs.

Interaction Between Device and Excitable Tissue, Other Than Transport

The interaction between device 100 and the molecule may extend beyond transport. For example, one or more of the following effects can be achieved instead of or in addition to transport:

(a) Device 100 applies fields that counteract or avoid negative effects of the molecule. As a result, molecules with a higher toxicity may be used, used at a higher dosage and/or used in a less rigidly monitored situation. In one example, device 100 applies fencing or tissue desensitizing fields, as described in some of the above applications, to prevent propagation of undesirable activation potentials in the heart. In another example, device 100 applied fields which reduce conduction velocity in tissue whose conduction velocity is undesirably increased by the provision of a drug. Alternatively, the molecule may serve to prevent or counteract an adverse effect of the non-excitatory control pulse.

(b) The molecule may be provided to avoid or counter act negative effects of the applied fields. The fields in question may be excitatory or non-excitatory. In one example, a molecule is provided to prevent or counteract edge effects at the fringes of applied non-excitatory fields.

(c) Device 100 applies fields that synergistically interact with the molecule. In one example, each of the molecule and the field work to increase cardiac contractility, and the combination is synergetic. One such exemplary molecule is caffeine. Another example of synergistic interaction is provided by Dobutamine (an example of an adrenergic agonist).

(d) Device 100 applies fields which prepare a portion of the heart for an applied molecule. Such preparation may include, for example, relaxation to allow better transport by an electric field, or without one. Another example is prevention or provision of blood flow to a portion of the heart, by manipulation the cardiac activation profile, Thus, a transport-related electric field may be applied before any molecule is provided. Another example of preparation is keeping a segment of the heart from contracting so that it has more available energy to respond to a drug. In another example, the electric fields may be applied to extend the duration of a cardiac cycle, to allow more time for transport of a molecule between beats or to allow more time for the molecule to take effect. In another example, a blood vessel wall is stimulated or relaxed to assist or otherwise modulate the transport through the vessel wall. Such control is especially useful for preventing the transport of a molecule in an undesired vector. The transport related field may be applied near the location of the transport filed or at a remote location. For example, a field that dilates or contracts blood vessels may be applied to control the flow of blood through the area being treated or the molecule provision area. In some embodiments of the invention, vascular control is provided independent of transport pulses and/or molecule provision.

(e) Device 100 applies fields, which by themselves do not interact with the molecules, but, as part of a complete control scheme, both these fields and the molecule act together to effect a desired control of the heart. In one example, a drug may be used to reduce overall conduction velocity in a ventricle, while an electric field is applied to increase the velocity at a certain location in the ventricle. In another example, a locally provided molecule is used to stimulate angiogenesis, while an electric field is used to reduce the work performed by the treated tissue, to allow it to receive and/or have available energy for the angiogenesis.

The size of the area and/or volume to which a non-excitatory electric field is applied may coincide with the molecule-affected area. Alternatively, it may be smaller, for example to apply a desired local effect or larger, for example, to counteract fringe effects. Alternatively, the electric field may be applied to a significant portion of the heart, for example to most of a ventricle, for example to enhance a stroke volume. Possibly, the molecule is used to interact with a defibrillation field. By selectively applying the electric fields and/or the molecules, spatial and/or temporal selectivity of the above effects may be achieved.

In some embodiments of the invention, there may be no interaction between the molecule and the other electric fields applied by device 100.

Calibration

Device 100 may be programmed and/or have parameters selected to match a particular patient (described below). Alternatively or additionally, one or more of a set of programs may be selected to be applied by device 100.

In an exemplary embodiment of the invention, prior to activating a treatment function of device 100, the patient state is evaluated, to determine a desirable treatment. In some embodiments of the invention, this evaluation is performed using device 100, in a purely sensory mode, or, optionally, with device 100 applying test treatments and determining their effects. Alternatively or additionally, various external stimuli may be provided, for example pharmaceuticals and their effects and/or interactions with device 100 monitored by device 100 and/or other apparatus.

During evaluation, one or more of the following regional pathologies may be identified: Scar, Hibernation, Ischemic and/or HR dependent ischemia. The identification may use various imaging methods, for example ECHO for hypo/dis/a-kinesis of ventricular walls. Various method may be used to evaluate perfusion, for example Technetium based imaging. Position sensing based methods may be used to evaluate regional function, for example systems provided by the Biosense Inc. corporation and/or ECG systems. These methods could be used to design and focus the treatment to the regions of interest.

Device Programming

In an exemplary embodiment of the invention, device 100 is programmed or otherwise controlled to provide a desired spatial and/or temporal regimen to the heart. Such a regimen can define which part of the heart is treated with which molecule and/or electrical field for what duration and under what circumstances. Such programming may be done in advance of implantation and/or therapy or it may be provided into device 100 just before or during therapy. In some embodiments of the invention, device 100 is used for experimental use, for example to determine which electric fields and/or molecules and/or combinations thereof have desirable therapeutic effects. Such a determination may be applied during product design or even when planning a therapeutic plan for a patient, as described herein.

Programming input 136 (FIG. 2) may be used for providing input from an external programmer. Device 100 may be non-autonomous, in that all programming comes from outside. Alternatively, a semi-autonomous device may be provided, in which external programming is required only on occasion, possibly at the instigation of device 100.

As can be appreciated, different transport fields and/or different molecules may be used for different heart rates, stroke volumes and/or as a function of other cardiac parameters. Depending on the desired effect of the molecule, the cardiac parameters taken into account may be local parameters, such as conduction velocity or global parameters, such as heart rate. The cardiac parameters may be rapidly changing parameters, such as heart rate or they may be slowly changing parameters such as tissue performance, Perfusion and/or viability, or maximum diastolic extension over a period of time. In some cases, the programming responds to non-cardiac parameters, such as time of day or day of the week, for example to match the therapy to an expected or current activity level.

Various device parameters may be programmable, including, for example, pulse parameters such as temporal, spatial, amplitude, polarity, envelope and/or frequency of the applied transport, transport related, excitatory (e.g., pacing) and/or non-excitatory fields. Alternatively or additionally, various molecule provision parameters may be controllable, for example the molecule type, timing of provision, amount provided and duration. In some devices, a complete script (e.g. a short program) may be selected or programmed. Alternatively or additionally, script parameters may be selected. A particular example of a script parameter is which sensor to use for monitoring and its associated threshold levels or other value-response function.

The programming may be enhanced by providing feedback about the operation and effects of device 100. The information may be sensed and/or stored by device 100 for later readout by the programmer. Alternatively, the information may be gleaned using other physical examination techniques, for example medical imaging.

Exemplary types of feedback include one or more of: feedback on molecule provision and penetration, various actually realized fields, the effect of such fields for transport or on cardiac tissue and/or the effect of the provided molecule, on the local tissue, the heart and/or the circulatory system as a whole. Alternatively or additionally, feedback on the quality and degree of synchronization between the heart, molecule provision and/or the various electrical fields, may be desirable. Exemplary sensors are described below.

In an exemplary embodiment of the invention, feedback is provided with regard to the penetration of the molecules. By using local sensing electrodes, the arrival of the molecules at the desired tissue depth can be monitored by detecting the effect of the molecules. Alternatively or additionally, by transporting radioactive or other marker drugs, it is possible to image or otherwise view the tissue and determine which cells were affected. A marker drug may be the same as the one used for therapy or it may be a different one, specifically selected for ease of detection. Alternatively or additionally, the provision and/or effect of molecules may be detected by applying an electric field to the treated area and based on the response of the tissue estimate the molecule effect and/or arrival.

In some cases, real-time feedback is desired, either to control device 100 in operation or to adjust programming parameters based on their effect. It should be noted that different types of feedback may be required for slow acting and for fast acting molecules. Some molecules may be double acting—having an effect that can be detected immediately, useful for verifying penetration and also having a long term effect. Fast acting molecules or drugs with a fast onset may require fast responding sensors. Slow acting drugs or drugs with a gradual onset may require sensors which average over several cardiac cycles and/or a processor associated with the sensor for processing the input therefrom.

One or more sensors (in some cases the field application electrodes can double as sensors) may be used to provide an indication of the heart's current status or its response to certain treatments. Exemplary sensors are described below.

Sensors

Various sensors may be used in conjunction with and/or as part of device 100. Such sensors may measure various cardiac parameters, including, for example, $pCO_2$, $pO_2$pH, $SO_2$, wall motion, local or global electrical activity, endocardial acceleration, regional impedance, regional APD, HR variability, LVP or aortic pressures (peak, max dP/dt), respiration rate, cardiac output and/or thoracic impedance (for estimating changes in stroke volume). Many such suitable sensors are known in the art. Alternatively or additionally, the sensors may measure systemic parameters, such as blood pressure. Alternatively or additionally, the sensors may measure local molecule concentrations and/or metabolic products.

The sensors may be implanted in the body. Alternatively, in some embodiments, the sensors maybe outside the body, even if device 100 is inside the body.

In some embodiments of the invention, the patient himself serves as a sensor, for example indicating to device 100 or its external programmer, body feelings, such as pain, shortness of breath, dizziness and/or lack or abundance or energy.

Safety

In some exemplary embodiments of the invention, device 100 may include one or more of the following safety features:

(a) Toxicology watchdog. This type of watchdog monitors one or more cardiac parameters and/or the response of the heart to various stimuli, to determine if the supplied molecules have an adverse effect on the heart. As a result, protective measures, such as fencing, may be applied, or the dosage or other parameters of drug delivery may be modified.

(b) Defibrillation circuit. Upon detection of defibrillation and/or VT, this circuit can apply a defibrillation current to the heart. Such a defibrillator may have charged capacitors continuously available in a standby mode. When not required for fibrillation, some of the charge may be used for applying large non-excitatory fields, for example for molecule transport.

(c) Molecule flow monitor. This monitor checks that the supply rate of the molecule matches the programmed supply rate. Thus, blockages and/or leaks may be detected. The monitor may directly monitor the flow and/or the molecule reservoir state. Alternatively, the monitor may determine the supply rate indirectly by analyzing cardiac and/or other patient physiological parameters.

(d) Fences. Non-excitatory electric fields may be used to create fences in the heart which prevent the propagation of undesirable (expected or not) activation potentials. Such field may act, for example, by desensitizing cardiac tissue using a DC field or by extending a refractory period of the cells by applying an electric pulse during an end of the refractory period.

(e) Beat capture. Various pacing schemes may be applied to increase the capture of the heart rate by the pacing signal and to avoid certain types of arrhythmia Exemplary Applications In one example, a heart is remodeled, by providing genetic material or other molecules which cause certain parts of the heart to atrophy or enlarge. In another example, the activation of the heart is modeled, for example by causing a cell type, such as an AV node cell, to increase its conduction velocity, for example by suitable over-expression or under-expression of certain ion pumps or channels. Other cell parameters which may be changed using this method include sensitivity (to hormones electrical signals and/or other feedback loops in the heart), plateau duration, excitation window duration and self-pacing rate (SA node).

In another example, at least certain types of long QT syndrome patients are treated by causing the expression of suitable ion channels or pumps to those cells that require it. This expression can be caused by providing the gene that creates the channels or creates a protein that transports the channels to the cell membrane, as well as by blocking a gene which stops the production of the channel.

In a post ischemic-event treatment application, drugs for maintaining the dilation of blood vessels or drugs for reducing oxygen requirements may be applied. In addition, molecules damaged or destroyed by the ischemic event may be provided by electrical transport techniques.

In an angiogenesis application, hormones and/or other angiogenesis factors are electrically transported to ischemic tissue and/or other tissue in the heart to cause increased blood vessel generation. In a particular application, repeated transport pulses, possibly from different electrodes are used to maintain a particular volume distribution of the provided molecule(s). In one example, these molecules define a gradient along which blood vessels or other tissue grow, or various cells, such as lymphocytes, travel. In another example, this distribution defines an area into which new growth will not enter.

In a related application, VEGF and/or other growth factors are locally provided, to prevent their adverse effects on other parts of the heart and/or body.

In another exemplary application, a locally provided molecule is Adriamycin or other chemotherapy anti-cancer molecules.

In a slow ablation application, a drug which suspend activity of a heart cell is applied to points of a mesh electrode. After detecting the effects of suspension on the electrical activity of the heart, an electrode having a desired effect is used to provide a killing dose of the same drug or of a different drug. Alternatively, selective ablation is possible even without first determining the effect of a "suspending" drug.

Figure 6:
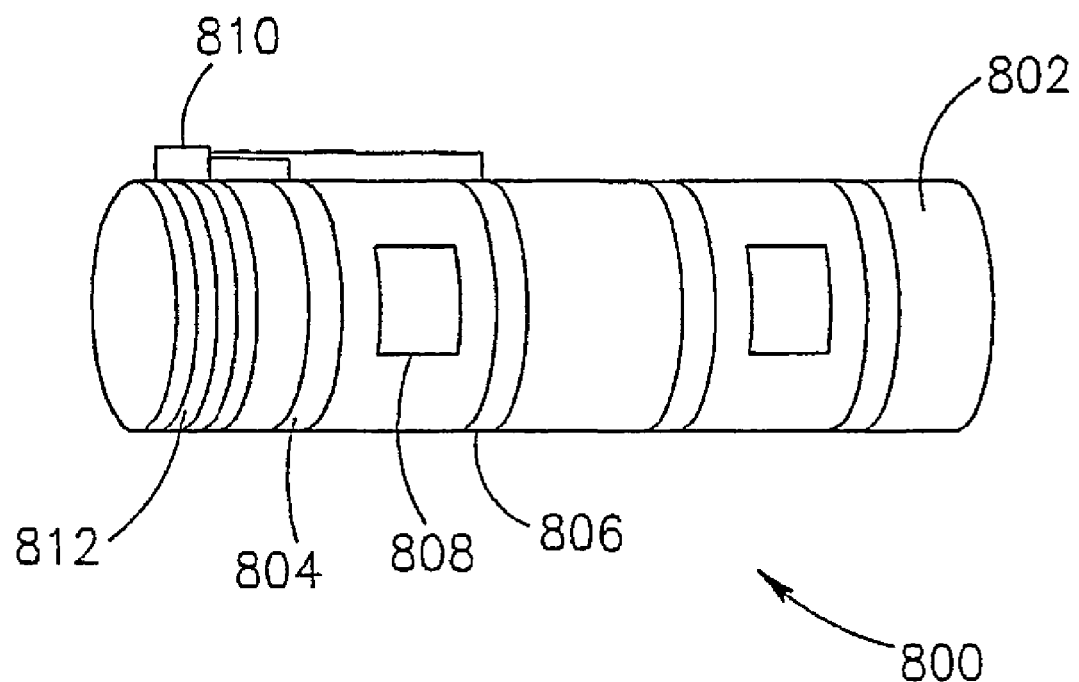
FIG. 6 illustrates a vascular treatment device, in accordance with an exemplary embodiment of the invention.

FIG. 6 illustrates a vascular treatment device 800, in accordance with an exemplary embodiment of the invention. In a coronary vessel application, iontophoresis and electroporation become possible in blood vessels which are near the heart. Example treatments include anti-clotting drugs, drugs to prevent re-stenosis, drugs to prevent stenosis and gene therapy to convert the blood vessel cells to those having a desired function, such as excretion of a desired anti-clotting factor. Such an electric field may be applied using a dedicated suitable stent or to augment the behavior of a stent which needs to be implanted. Exemplary device 800 is stent-like, having a cylindrical body 802. A plurality of electrodes 804 and 806 are provided, which are electrified by a power supply 810. In one embodiment of the invention, the power supply is a battery. Alternatively or additionally, the power supply comprises an antenna 812 for receiving RF radiation and a converter for converting the received radiation in suitable voltages. Alternatively or additionally, power supply 810 include control logic and/or one or more sensors, for example for sensing a cardiac activity, for example for synchronization purposes or a sensor for sensing the blood vessel state. Optionally, electrodes 804 and 806 can serve as antenna 812. Alternatively, a wired external power source is provided and connected to device 800. In some embodiments, device 800 is used with blood vessels not adjacent to the heart. In some embodiments of the invention, antenna 812 also serves to apply a voltage across the vessel in which device 800 is situated.

An exemplary configuration for transmitting power by RF radiation, to a stent-like device, which may store the energy in a capacitor, is shown in PCT publication WO 99/55360 to Medtronic, et al., the disclosure of which is incorporated herein by reference. The actual levels of power and/or voltage required in device 800 may be higher, possibly requiring a straightforward design modification and/or a voltage converter in device 800. RF radiation may also be used to send commands to device 800.

In an exemplary embodiment of the invention, a molecule reservoir 808 is provided between two adjacent electrodes, for example on an outside surface of body 802. When a voltage potential is formed between electrode 804 and electrode 806, the molecule is transported from reservoir 808. The molecule may then diffuse into a surrounding wall of a blood vessel. Alternatively or additionally, the voltage field between the electrodes has a sufficient component to transport the molecule perpendicular to device 800. Alternatively or additionally, the voltage field opens pores in the vessel wall to enhance the diffusion of the molecule.

In an alternative embodiment, device 800 comprises two or more layers, with one polarity electrode in one layer and a second polarity electrode in the other layer.

In another alternative embodiment, device 800 is mounted outside the blood vessel. In such a case, a cylindrical body shaped like body 802 in the figure may not be required, so wireless patch-shaped electrodes may be provided instead.

In another exemplary embodiment, a work increasing excitatory (e.g., over pacing) or non-excitatory (e.g., contractility enhancing) pulse is applied to provide oxygen stress, while, at a same time, angiogenesis enhancing molecules are provided, locally or systemically.

In another exemplary embodiment, the salvage of ischemia-damaged tissue is enhanced by both reducing its oxygen requirements using a desensitizing electric field (or fences) and by locally providing work-reducing molecules, such as calcium blockers. In some embodiments, the calcium blockers are systemically provided in a form that has difficulty crossing blood vessel walls. By application of a local field, the calcium blockers affect substantially only the treated area. In some cases, the molecule and the electric field are applied simultaneously. In other cases, they are alternated, for example to allow the tissue to recuperate from adverse effects of one or the other. Once the tissue has sufficiently recuperated, it may be trained back to shape and/or have angiogenesis enhancing methods applied to it.

In another exemplary embodiment, hypertrophy of a part of the heart is treated by applying a suitable electrical control sequence to reduce the cardiac activity of the part and applying a molecule to reduce the hypertrophy.

Circulating Reservoir

In an exemplary embodiment of the invention, the device is used to release a molecule from a circulating reservoir. In an exemplary embodiment of the invention, the device is stent-like, for example as shown in FIG. 6. Alternatively, the device may comprise electrodes inside or outside the blood vessel.

In an exemplary embodiment of the invention, the reservoir comprises a plurality of liposomes that encapsulate a molecule.

U.S. Pat. No. 6,041,252 to Walker et al., the disclosure of which is incorporated herein by reference, describes liposome compositions and field strengths that will cause the liposomes to release their contents and/or migrate towards the walls of a blood vessel. Also described is a non-toxic material for sealing temporary pores formed in body cells as a result of the applied field. Also described are various therapeutic materials. Alternatively or additionally, non-electrical means may be used to free the molecule from the liposome, for example, chemical means secreted by the device into the blood flow, for example Nystatin that forms pores in liposomes, special molecules for liposomes designed to be opened by chemical means and/or other means, such as heating means, or optical means, for suitably sensitive liposomes.

Referring back to FIG. 6, device 800 may include electrodes for applying a field across the blood vessel, to release molecules from a circulating reservoir, alternatively or additionally, to applying an iontophoresis field, an electrophoresis field and/or a field for releasing a molecule from reservoirs 808. The electrification of the electrodes and/or their layout may be different for the different effects, for example for liposome release or migration, different polarity electrode elements may be provided on opposite sides of device 800, so that the field is applied across the blood vessel. For extraction from reservoir 808, a voltage between two nearby electrodes may be applied. In an exemplary embodiment of the invention, electrodes 804 and/or 806 comprise multiple parts, which can be selectively electrified to achieve various field directions and/or strengths under the control of controller 810.

A sensor in device 800 may be used to synchronize the application of the release and/or transport fields to local and/or global activity of the excitable tissue. Alternatively, other effects can be achieved by the fields, as described above. The transport field, the release filed and the control filed may be the same or different fields and/or two effects may be combined in a single field.

In an exemplary embodiment of the invention, device 800 is used to release molecules in the vascular bed of an organ to be treated, for example in a coronary artery of the heart or a renal artery. Alternatively or additionally, the molecules are released into a vessel that passes near the tissue to be treated. Alternatively or additionally, the molecules are released in the vessel, to be transported, (e.g., electrically) through the vessel walls into nearby tissue.

Reservoir 808, or multiple reservoirs, may include a same molecule or different as in the circulating reservoir. Alternatively or additionally, multiple reservoirs with different materials may be provided. Optionally, non-electrical release from reservoir 808 is used. At least one or the reservoirs in device 800 may be pointed inwards, to release its contents into the blood stream. Alternatively or additionally, it may be pointed outwards, to release its contents into the vessel wall. Alternatively or additionally, the release direction may be controlled by the particular transport electric field applied. In a non-stent device, the reservoir may be provided and/or activated separately from the electrodes.

In an exemplary embodiment of the invention, the locally released molecule may interact with a systemically available molecule. In one example, the locally available molecule is an antagonist for the systemic molecule, so that the systemic molecule has a different or no effect locally (e.g., Heparin and its antagonist Protamine). Alternatively or additionally, the systemic molecule prevents the local molecule from having an effect away from where it is released, for example, due to the lower concentration of the local molecule. Alternatively, an enhancement effect may be provided, with the local molecule enhancing or activating the systemic molecule, or vice versa. The systemic molecule may be provided as a circulating reservoir or by injection or other means. Thus, in some embodiments of the invention, the systemic molecule is released locally, together with another locally released molecule from device 800.

In another example, device 800 is used to genetically modify (e.g., by eluting viruses or direct electrophoresis of DNA) the vascular tissues. These modified tissues may elut a chemical that interacts with the systemic drugs (or otherwise provided molecule). Alternatively or additionally, the modified cells may include fewer or a greater number of receptors (or other reason for sensitivity) for the systemic drug. Alternatively or additionally, the modified cells may exhibit a higher or lower uptake or transport rate for the drug.

In an exemplary embodiment of the invention, two sensors are provided, one at the entrance to the targeted tissue and one at a different location, for example elsewhere in the vascular system or at the vascular exit from the targeted tissue. The second sensor, which may also be mounted on a stent, possibly a molecule releasing stent, may measure the amount of the released molecule in the blood stream. The measurement may be direct, or a easily detectable tag may be released with the molecule.

Such measurement may be applied during testing of dosage or during calibration or regular use of device 800. For example, the second device may indicate to the user that the level of circulating molecule is too high (or too low). Alternatively or additionally, the second device may automatically elute an antagonist to the molecule secreted by the first device. Optionally, such automatic secretion is performed without a sensor, for example, based on calibration of the device or by external activation.

Non-Cardiac Applications

The above application has focused on cardiac applications. It should be noted that similar devices may be used for non-cardiac applications, in whole organs or in portions of excitable or non-excitable tissues. It should be noted that the heart typically has two properties not found in other excitable tissue: synchronous operation and significant and immediate health risk due to adverse effects. The brain for example, as a whole, does not exhibit unitary synchronized behavior as does the heart. The stomach on the other hand, while it is synchronous, does not pose immediate life-threatening danger as a result of adverse effects. However, many non-cardiac tissue may cause discomfort (sort or long term) and/or pain, if incorrectly activated. Thus, in some cases, an excitatory transport or release pulse may be used. Alternatively or additionally, the electric fields applied are synchronized to the activation in the excitable tissue. Alternatively or additionally, a propagation stopping field (fencing) may be used to prevent propagation of the effects of the transport pulse.

It should be noted that some excitable tissues may be relaxed by application of a suitable non-excitatory or excitatory pulse, thus possibly assisting transport. Alternatively or additionally, the pulse may target excitable components of the tissue, for example blood vessels. Alternatively or additionally, the electric field may be applied to stiffen excitable tissue, thus preventing molecule uptake.

In some embodiments of the invention, the application of electrical field and/or molecules ignores the excitatory (or excitation disruption) effect of the electric field, but uses other features described herein, for example multiple vectored molecule distribution using electrode arrays, reduction of blood flow or implantable wireless electrodes having associated therewith molecule reservoirs. Alternatively, non-pain causing effects, such as muscle contractions, or even pain causing effects, such as muscle spasms may be ignored or taken into account when applying the fields. It is noted that also some cardiac applications can allow the transport field to be excitatory., One exemplary application is treatment of irritable bowel syndrome using locally transported anti-inflammatory drugs, such as steroids. The drugs and/or a transport-related signal possibly timed to the normal bowel electrical activity so as not to interfere with it. Alternatively or additionally, the electrical signal also controls the bowels. For bowel and other hollow organ applications, a device similar to that of FIG. 6 may be used. In an exemplary embodiment of the invention, the drugs are released in the upper or lower mesenteric arteries, to better target them to the bowels. Alternatively or additionally, a systemic inhibitor is provided, to reduce the effect of the drugs on tissues outside of the bowels.

In a pulmonary application, COPD and asthma are treated, for example, using adrenergic agonists, phosphodiesterase inhibitors, steroids and/or cholinergic antagonists. The electric fields may be selectively applied to prevent inadvertently affecting the heart.

In a urinary example, muscle relaxants to bladder are locally provided, for example at night, to treat overflow incontinence caused by an over excited bladder. A suitable implantable device may be, for example, a stent implanted inside the urethra. Local provision may prevent possibly systemic and/or organ specific side effects of smooth muscle relaxants, for example, hypotension, digestive problems and/or cardiac effects.

In a joint application, gold or other lubricants are transported into a joint, for example with the electric field synchronized to prevent inadvertent electrical activation of muscles.

In a non-cardiac angiogenesis application, the growth of new vessels in an organ is provided by targeting VEGF (or other growth factors) to that organ or part thereof, for example, to combat or prevent diabetes-related gangrene.

In a uterine application, uterine contractions are suppressed during labor, or during an early labor, using targeted tocolytic drugs and/or suitable electrical pulses. Alternatively, contractions are enhanced and/or controlled while and/or shortly after providing a drug. Optionally, the uterus is relaxed when the drug is provided, to assist in tissue penetration. Alternatively or additionally, the uterus may be contacted after the provision, to enhance delivery.

In a skeleton muscle example, muscle relaxants may be supplied, locally to a muscle limb and/or a part thereof.

Targeted Protection

In an exemplary embodiment of the invention, protection of an organ from a system effect is supplied by providing, at a vascular entrance to organ, a device that releases antagonist molecules. The release may be synchronized to the availability of systemic molecules, for example, both being controlled by a same controller. Any type of release mechanism may be used, including electrical and non-electrical mechanisms. In a particular example, the kidney is protected from cyclosporine, an anti-rejection drug, which may provided for preventing rejection of an implanted heart.

Alternatively or additionally, the system may be protected from a molecule targeted to a particular tissue, for example, by releasing the antagonist at the vascular exit from the tissue. For example, an antagonist for a cardiac stimulator, at the exit from the coronary vessels. Alternatively or additionally to chemical antagonists, antibodies may be used for tagging and/or activity prevention. Tagging may be used for collecting information about dosages and its effects and/or for stimulating removal by the pagocytic system.

In another example, a suitable antagonist is used to counteract toxic effects of a molecule used to release a drug from a liposome.

In another exemplary embodiment of the invention, a systemic., less active molecule is provided, with an activator being released at a vascular entrance to an organ and/a deactivator being released at the vascular exit from the organ.

Multi-Treatment Kit

In an exemplary embodiment of the invention, the device (e.g., device 800) is provided as a kit that may be used with a variety of molecules, organs, treatment protocols and/or systemic provision protocols. The kit may include, for example, a stent and an external controller, for providing programming of the stent and/or real-time control of the stent. Optionally, such a kit includes multiple stents, for example for providing an activator/deactivator pair of molecules.

In some embodiments, a multi-catheter system is used to provide multiple types of molecules and/or multiple electrode locations.

It will be appreciated that the above-described methods of transporting molecules in the various tissues may be varied in many ways. In addition, a multiplicity of various features, both of methods and of devices has been described. Where methods are described, devices for carrying out the methods are also contemplated. It should be appreciated that different features may be combined in different ways. In particular, not all the features shown above in a particular embodiment are necessary in every similar exemplary embodiment of the invention. Further, combinations of the above features are also considered to be within the scope of some exemplary embodiments of the invention. Also within the scope of the invention are devices and/or software for programming existing devices to make the device comply with the methods described herein. Section headings where they appear are meant for clarity of browsing only and should not be construed as limiting the contents of a section to that particular section. When used in the following claims, the terms "comprises", "includes", "have" and their conjugates mean "including but not limited to".

It will be appreciated by a person skilled in the art that the present invention is not limited by what has thus far been described. Rather, the scope of the present invention is limited only by the following claims.

The invention claimed is:

1. Electrical treatment apparatus for use with an associated molecule source, comprising:
at least one electrode;
a power source for electrifying said at least one electrode; and
a controller, which is programmed to activate the power source to selectively electrify said at least one electrode to apply at least one electric field, said at least one electric field having a transport effect for transporting a molecule in a desired manner and a non-excitatory control effect, which does not induce an additional propagating action potential, for controlling the activity of at least a part of a non-cardiac excitable tissue, said programming selected to achieve a desired provision of said molecule into said at least a part of an excitable tissue or associated vasculature, said desired provision being at least assisted by an interaction between the transport effect and the control effect.

2. Apparatus according to claim 1, wherein said controller is hardware programmable.

3. Apparatus according to claim 2, comprising a wireless programming input.

4. Apparatus according to claim 1, wherein said controller is software programmable.

5. Apparatus according to claim 1, wherein said programming comprises programming adapted for a patient.

6. Apparatus according to claim 1, wherein said programming comprises a setting of at least one operational parameter of said apparatus.

7. Apparatus according to claim 1, wherein said programming comprises a selection or at least one operational protocol from a set of available protocols in said apparatus.

8. Apparatus according to claim 1, wherein said controller is operable in a testing mode, in which mode a test treatment of a molecule is provided to the patient and the response of the patient to the test is monitored by said controller.

9. Apparatus according to claim 1, comprising a synchronization connection to said molecule source.

10. Apparatus according to claim 9, wherein said synchronization connection comprises an informative connection that provides at least one informative signal to said controller, informing of a state of molecule release.

11. Apparatus according to claim 9, wherein said synchronization connection comprises a control connection that provides at least one control signal from said controller, to control a state of molecule release.

12. Apparatus according to claim 11, wherein said molecule source is an electric-field mediated molecule source and wherein said control signal generates an electric field that releases said molecule from said source.

13. Apparatus according to claim 12, wherein said synchronization connection is comprised in said at least one electrode used for applying a transport effect.

14. Apparatus according to claim 13, wherein said molecule source is integral with said electrode.

15. Apparatus according to claim 13, wherein said molecule source comprises blood dispersed molecules.

16. Apparatus according to claim 1, wherein said molecule source is integral with said at least one electrode used for applying a transport effect.

17. Apparatus according to claim 1, wherein said molecule source is integral with said apparatus.

18. Apparatus according to claim 1, wherein said molecule source is external to said apparatus.

19. Apparatus according to claim 1, wherein said molecule source comprises a catheter, coupled to said apparatus outside a patient.

20. Apparatus according to claim 1, wherein said molecule source comprises a source of a plurality of molecule types.

21. Apparatus according to claim 20, wherein said controller controls said molecule source to selectively release at least a particular one of said plurality of molecule types.

22. Apparatus according to claim 1, comprising at least one sensor that senses a functional tissue parameter and provides said sensed parameter to said controller.

23. Apparatus according to claim 22, wherein said sensor measures a functional tissue parameter relating to the entire excitable tissue.

24. Apparatus according to claim 22, wherein said sensor measures a functional tissue parameter relating to a portion of the excitable tissue.

25. Apparatus according to claim 22, wherein said controller is configured to analyze said sensed parameter to detect an effect of said molecule on said excitable tissue.

26. Apparatus according to claim 22, wherein said controller is configured to analyze said sensed parameter to detect an activity of the excitable tissue and wherein said controller synchronizes said provision to said sensed activity.

27. Apparatus according to claim 22, wherein said controller is configured to analyze said sensed parameter to detect an effect of said field on said excitable tissue.

28. Apparatus according to claim 22, wherein said controller modifies said at least one electric field to modify said transport effect responsive to said sensed parameter.

29. Apparatus according to claim 22, wherein said controller modifies said at least one electric field to modify said control effect responsive to said sensed parameter.

30. Apparatus according to claim 22, comprising a watchdog that detects an abnormal effect of said applied fields.

31. Apparatus according to claim 22, comprising a watchdog that detects an abnormal effect of said molecule.

32. Apparatus according to claim 1, comprising a user input for receiving an indication of an effect of said apparatus from a patient.

33. Apparatus according to claim 1, wherein a single electric field applies both of said transport effect and said control effect.

34. Apparatus according to claim 1, wherein said at least one electric field comprises at least one transport field and at least one control field.

35. Apparatus according to claim 1, wherein said transport effect and said control effect are provided simultaneously.

36. Apparatus according to claim 1, wherein said transport effect and said control effect arc applied sequentially.

37. Apparatus according to claim 1, wherein said control effect is selectively applied in association with only some of said transport effects.

38. Apparatus according to claim 1, comprising at least one pacing electrode that is controlled by said controller to apply a pacing pulse.

39. Apparatus according to claim 38, wherein said at least one pacing electrode is comprised in said at least one electrode.

40. Apparatus according to claim 1, wherein said transport effect is provided by an excitatory field.

41. Apparatus according to claim 1, wherein said transport effect is provided by a non-excitatory field.

42. Apparatus according to claim 1, comprising an output port for generating an output to a patient.

43. Apparatus according to claim 1, wherein said control effect is selected to prevent an adverse effect of said pulse.

44. Apparatus according to claim 1, wherein said control effect is selected to prevent an adverse effect of said molecule.

45. Apparatus according to claim 1, wherein said molecule is selected to counteract an adverse effect of said control effect.

46. Apparatus according to claim 1, wherein said control effect is selected to counteract an adverse effect of said molecule.

47. Apparatus according to claim 1, wherein said control effect is selected to prepare said tissue for said transport.

48. Apparatus according to claim 1, wherein said control effect is selected to extend a period of time suitable for provision of said molecule.

49. Apparatus according to claim 1, wherein said control effect and said molecule are selected to cooperate and effect a desired treatment of said tissue.

50. Apparatus according to claim 1, wherein said at least one electrode comprises at least one transport electrode for applying a transport effect of said at least one field and at least one control electrode for applying said control effect of said at least one field.

51. Apparatus according to claim 1, wherein said transport effect and said control effect of said at least one electric field are applied using at least one common electrode of said at least one electrode.

52. Apparatus according to claim 50, wherein said at least one control electrode is spatially displaced from said at least one transport electrode.

53. Apparatus according to claim 1, wherein said at least one electrode comprises a point electrode.

54. Apparatus according to claim 1, wherein said at least one electrode comprises a spiral electrode.

55. Apparatus according to claim 1, wherein said at least one electrode comprises a linear electrode.

56. Apparatus according to claim 55, wherein said electrode comprises a plurality of independently electrifiable contacts.

57. Apparatus according to claim 56, wherein said controllers selectively electrifies said independent contacts to achieve a desired, non-uniform, volumetric dispersion of said molecule, relative to said electrode.

58. Apparatus according to claim 1, wherein said at least one electrode comprises a mesh electrode.

59. Apparatus according to claim 1, wherein said at least one electrode comprises a plate electrode.

60. Apparatus according to claim 1, wherein said at least one electrode is connected by wire to said controller.

61. Apparatus according to claim 1, wherein said at least one electrode is a wireless electrode.

62. Apparatus according to claim 1, wherein said at least one electrode is implantable.

63. Apparatus according to claim 1, wherein said at least one electrode is mounted on a catheter.

64. Apparatus according to claim 1, wherein said at least one electrode is an external electrode.

65. Apparatus according to claim 1, wherein said apparatus is implantable.

66. Apparatus according to claim 1, wherein said apparatus comprises a cylindrical body adapted for implantation inside a blood vessel.

67. Apparatus according to claim 1, wherein said apparatus is wholly external to the patient.

68. Apparatus according to claim 1, wherein said transport effect comprises iontophoresis.

69. Apparatus according to claim 1, wherein said transport effect comprises electroporation.

70. Apparatus according to claim 1, wherein said non-cardiac excitable tissue comprises uterine tissue.

71. Apparatus according to claim 1, wherein said non-cardiac excitable tissue comprises bladder tissue.

72. Apparatus according to claim 1, wherein said non-cardiac excitable tissue comprises digestive tissue.

73. Apparatus according to claim 1, wherein said transport effect comprises releasing a molecule from a circulating reservoir.

74. Apparatus according to claim 73, wherein said circulating reservoir comprises liposomes in a blood stream.

75. Apparatus according to claim 1, wherein said controller coordinates the interaction of a systemic molecule and locally available molecule, to have a synergistic effect.

76. Apparatus according to claim 75, wherein said local molecule blocks an effect of said systemic molecule.

77. Apparatus according to claim 75, wherein said local molecule enhances an effect of said systemic molecule.

78. Apparatus according to claim 75, wherein said systemic molecule blocks an effect of said local molecule away from said a locality where said local molecule is provided.

79. Apparatus according to claim 75, wherein said systemic molecule enhances an effect of said local molecule.

80. Electrical treatment apparatus for use with an associated molecule source, comprising:

at least one electrode;

a sensor for sensing a functional state of a non-cardiac tissue;

a power source for electrifying said at least one electrode; and a controller, which is programmed to activate the power source to selectively electrify said at least one electrode to apply at least one non-excitatory electric field; said electric field having a transport effect, which does not induce an additional propagating action potential, for transporting a molecule in a desired manner, synchronized to said sensed functional state.

* * * * *